(12) United States Patent
Brasile

(10) Patent No.: US 6,642,045 B1
(45) Date of Patent: Nov. 4, 2003

(54) SYSTEM FOR EXSANGUINOUS METABOLIC SUPPORT OF AN ORGAN OR TISSUE

(75) Inventor: Lauren Brasile, Albany, NY (US)

(73) Assignee: Breonics, Inc., Otisville, NY (US)

( * ) Notice: Subject to any disclaimer, the term of this patent is extended or adjusted under 35 U.S.C. 154(b) by 0 days.

(21) Appl. No.: 09/547,843

(22) Filed: Apr. 12, 2000

Related U.S. Application Data
(60) Provisional application No. 60/129,257, filed on Apr. 14, 1997.

(51) Int. Cl.[7] .................................................. A01N 1/02
(52) U.S. Cl. ...................................... 435/284.1; 435/1.2
(58) Field of Search ............................... 435/1.2, 284.1; 422/45–48

(56) References Cited

U.S. PATENT DOCUMENTS

| | | | | |
|---|---|---|---|---|
| 3,632,473 A | * | 1/1972 | Belzer et al. | 435/1.2 |
| 3,639,084 A | * | 2/1972 | Goldhaber | |
| 4,033,825 A | * | 7/1977 | Haddad et al. | 435/286.6 |
| 5,051,352 A | * | 9/1991 | Martindale et al. | |
| 5,484,789 A | | 1/1996 | Thurman et al. | 514/277 |
| 5,552,267 A | | 9/1996 | Stern et al. | 435/1.1 |
| 5,584,804 A | | 12/1996 | Klatz et al. | 604/24 |
| 5,716,378 A | | 2/1998 | Minten | |
| 5,747,469 A | * | 5/1998 | Roth et al. | 514/44 |
| 6,046,046 A | * | 4/2000 | Hassanein | 435/284.1 |
| 6,100,082 A | | 8/2000 | Hassanein | 435/284.1 |

FOREIGN PATENT DOCUMENTS

| | | | |
|---|---|---|---|
| EP | 0 376 763 A2 | * | 7/1990 |
| WO | WO-88/05261 A1 | * | 7/1988 |
| WO | WO 93/00808 | | 1/1993 |
| WO | WO-96/29865 A1 | * | 10/1996 |

OTHER PUBLICATIONS

Hassanein, et al., "Continuous Perfusion of Donor Hearts in the Beating State Extends Preservation Time and Improves Recovery of Function", The Journal of Thoracic and Cardiovascular Surgery, 11/98, 821–830.

Lakey, et al., "Development of an Automated Computer-Controlled Islet Isolation System", Cell Transplantation, Vol 6 No. 1, 1997, 47–57.

(List continued on next page.)

Primary Examiner—William H. Beisner
(74) Attorney, Agent, or Firm—Heslin Rothenberg Farley & Mesiti P.C.; Kathy Smith Dias, Esq.

(57) ABSTRACT

An exsanguinous metabolic support system for maintaining an organ or tissue at a near normal metabolic rate is disclosed. The system employs a warm perfusion solution capable of supporting the metabolism of the organ or tissue thereby preserving its functional integrity. The system also monitors parameters of the circulating perfusion solution, such as pH, temperature, osmolarity, flow rate, vascular pressure and partial pressure of respiratory gases, and regulates them to insure that the organ is maintained under near-physiologic conditions. Use of the system for long-term maintenance of organs for transplantation, for resuscitation and repair of organs having sustained warm ischemic damage, as a pharmaceutical delivery system and prognosticator of posttransplantation organ function is also disclosed.

15 Claims, 2 Drawing Sheets

OTHER PUBLICATIONS

Nakamura, et al., "Ex Vivo Liver Perfusion with Arterial Blood from A Pig with Ischemic Liver Failure", Artificial Organs, 23(2), 1999, 153–160.

Dutkowski, et al., "Rat Liver Preservation by Hypothermic Oscillating Liver Perfusion Compared to Simple Cold Storage",Cryobiology, 36, 1998, Article No.: CY972066; 61–70.

Eschwege, et al., "Subzero Nonfrozen Storage of Rat Kidneys and Livers: Computer–Assisted Organ Perfusion–Storage Equipment", Transplantation Proceedings, Vol 28, No 5 Oct., 1996, 2900–2902.

Flax, et al., "Analogue Computer Model of a Kidney During Preservation", Med. & Biol. Eng. & Comput., 1979, 17, 199–206.

Adem et al., "Computer Control of a Modified Langendorff Perfusion Apparatus for Organ Preservation Using Cryoprotective Agents", J. Biomed. Engng., 1981, Vol 3, Apr., 134–139.

Vahl, et al., "Heterogeneity of Myocardial Edema in Isolated Pig Hearts after Perfusion with Different Types of Cardioprotective Solutions", Thorac. Cardiovasc. Surg. 46 (1998) 285–292.

Chen, et al., "Clinical Experience with a Porcine Hepatocyte–Based Liver Support System", The International Journal of Artificial Organs, Vol 19, No. 11, 1996, 664–669.

Fahy, et al., "Cryopreservation of Mammalian Kidney", Cryobiology 35, Article No. CY972026, 1997, 114–131.

* cited by examiner

SYSTEM FOR EXSANGUINOUS METABOLIC SUPPORT OF AN ORGAN OR TISSUE

CROSS-REFERENCE TO RELATED APPLICATIONS

This application claims the priority of U.S. application Ser. No. 60/129,257 filed Apr. 14, 1999, the entire disclosure of which is incorporated herein by reference.

FIELD OF THE INVENTION

The invention relates to a metabolic support system including a solution, method and apparatus for sustaining organs for transplantation under near-physiologic conditions. More particularly, the invention relates to use of the system for repair and/or long-term maintenance of organs for transplantation, as a pharmaceutical delivery system and prognosticator of posttransplantation organ function.

BACKGROUND OF THE INVENTION

There continues to be an extreme shortage of organs for transplantation. Currently, the major limiting factor in clinical transplantation is the persistent shortage of organs. For example, kidney transplantation is largely dependent upon the availability of organs retrieved from heart-beating cadaver donors. There exists, however, a large and as yet untapped source of organs for transplantation, namely, non-heart-beating cadavers. Non-heart-beating cadavers are accident victims who succumb at the site of an injury and those having short post-trauma survival times. Additionally, non-heart-beating cadavers result when families are emotionally unable to make the decision to donate the organs of a loved one contemporaneously with making the decision to terminate life support. In these situations, the organs are not used because the lack of circulating blood supply (warm ischemia) once the heart stops beating, results in an injury cascade.

An organ marginally, but functionally damaged by warm ischemia cannot tolerate further damage mediated by the hypothermic conditions presently utilized to preserve organs intended for transplantation. Under these conditions, the lipid bilayer experiences a phase-change and becomes gel-like, with greatly reduced fluidity. The essentially frozen lipid in the cell membranes negates the utilization of $O_2$-tension. The metabolic consequence is glycolysis, which is analogous to the state of anoxia. It has been described that below 18° C., hypothermia inhibits the tubular and glomerular activities of the kidney and that at 4° C., the utilization of oxygen is approximately 5% of that at normothermia.

Hypothermic storage can also produce vasospasm and subsequent edema in an organ. Hypothermically preserved organs can experience glomerular endothelial cell swelling and loss of vascular integrity along with tubular necrosis; phenomenon attributable to the hypothermic conditions employed. Hypothermia can also inhibit the Na/K dependent ATPase and result in the loss of the cell volume regulating capacity. The loss of volume regulation is what causes the cellular swelling and damage. An ample supply of oxygen does not actively diminish the amount of this swelling because the cell membrane is essentially frozen, preventing the effective utilization of oxygen. Without adequate oxygen delivery, the anoxia leads to disintegration of the smaller vessels after several hours of perfusion. The lack of oxygen and the subsequent depletion of ATP stores mean that anaerobic glycolysis is the principal source of energy under traditional preservation conditions. The subsequent loss of nucleosides is probably a very important factor in the failure of tissues subjected to warm ischemia and prolonged periods of cold ischemia to regenerate ATP after restoration of the blood supply. The inability to supply adequate oxygen has led to the routine reliance on hypothermia for organ preservation. In the case of warm ischemia, circulatory arrest leads to anoxia where there is no molecular oxygen for oxidative phosphorylation. The lack of molecular oxygen leads to the accumulation of NADH and the depletion of ATP stores with in the mitochondria.

Thus, ischemia (whether warm ischemia or cold ischemia) is an injury cascade of events that can be characterized as a prelethal phase, and a lethal phase. The prelethal phase produces harmful effects in three ways: hypoxia; malnutrition; and failure to remove toxic metabolic wastes. With the lack of circulating blood comes a lack of molecular oxygen. The resulting hypoxia induces depletion of energy stores such as the depletion of ATP stores in mitochondria. Depletion of ATP leads to cellular changes including edema, loss of normal cellular integrity, and loss of membrane polarity. The cellular changes, induces the lethal phase of ischemia resulting in accumulation of metabolic wastes, activation of proteases, and cell death.

The perfusate solution that represents the current state-of-the-art in hypothermic organ preservation, and provides for optimized organ preservation under hypothermic conditions, contains components which prevent hypothermic induced tissue edema; metabolites which facilitate organ function upon transplantation; anti-oxidants; membrane stabilizers; colloids; ions; and salts (Southard et al., 1990, Transpl. 49:251; and Southhard, 1989, Transpl. Proc. 21:1195. The formulation of this perfusate is designed to preserve the organs by hypothermic induced depression of metabolism. While it minimizes the edema and vasospasm normally encountered during hypothermic storage, it does not provide for the utilization of a substantially expanded donor pool.

This is due to the fact that an organ or tissue damaged by warm ischemia cannot tolerate further damage mediated by the hypothermia. Even with just 30 minutes of ischemic, the postransplant function of an organ can be compromised. For example, using organs from heart beating cadavers (non-damaged), the immediate nonfunction rate is estimated to be 25%; and within just 30 minutes of warm ischemia, the immediate nonfunction rate is increased to about 60%. Thus, 60% of the kidneys from non-heart-beating cadavers do not immediately function because of prelethal ishchemic injury. Further, irreversible ischemic damage and injury is thought to occur to organs deprived of blood flow in just a few hours or less (Klatz et al., U.S. Pat. No. 5,395,314). Unless new sources of organs can be developed, the number of transplantation procedures will remain constant. Additionally, the donor pool cannot be substantially expanded because there is no process/system available to repair prelethal ischemic damage in warm ischemically damaged organs or tissues.

Recent efforts have focused on prevention of ischem ic damage by intervening with a solution immediately upon cessation of blood flow. For example, a protective solution, disclosed in U.S. Pat. No. 4,415,556, is used during surgical techniques or for organs to be transplanted for preventing ischemic damage to the organ. The protective solution is used as a perfusate to improve aerobic metabolism during the perfusion of the organ. U.S. Pat. No. 5,395,314 describes a method of resuscitating a brain by circulating, after interruption of the blood supply, through the brain a hypothermic preservation solution (approximately 8–10° C.) designed to lower organ metabolism, deliver oxygen, and inhibit free radical damage.

Although such methods and preservation solutions are useful in preventing ischemic damage in organs, these beneficial effects are overshadowed by practical and functional limitations. First, for such methods and solutions to be effective in preventing ischemic damage, they must be applied immediately (within minutes) after interruption of the blood supply. Logistic restraints, as in the case where an accident victim becomes an organ donor, may severely curtail the use of such methods and solutions. For example, their use is impractical at the site of an accident or in the ambulance where initiation of the ischemic injury cascade would occur. Secondly, irreversible ischemic damage and injury is thought to occur to organs deprived of blood flow in minutes (e.g., brain) or within just a few hours (heart, kidney). An organ or tissue, marginally, but functionally, damaged by warm ischemia cannot tolerate further damage mediated by hypothermic storage prior to transplantation, or restoration of blood flow upon transplantation. One reason is that restoration of the circulation after ischemic-reperfusion may paradoxically result in further tissue damage. (McCord et al., 1985, N Engl J Med 312:159–163). During reperfusion, reoxygenation of ischemically damaged tissue can result in further tissue injury caused through the formation of oxygen free radicals, depletion of free radical scavengers, and the release of chemotactic agents.

Thus, there is a need for a system, including a preservation solution useful for initial organ flushing and as a perfusate for in situ or ex vivo preservation of organs for transplantation, which employs a warm preservation technology which minimizes, and, in fact, repairs damage due to warm ischemia, and which supports the organ near normal metabolic rate. Portability and automation of the system is important, particularly in situations where the system is used to initiate organ preservation in situ either prior to or immediately following termination of life support or at external sites following an accident where cardiac arrest has occurred.

SUMMARY OF THE INVENTION

In one aspect, the invention relates to an exsanguinous metabolic support system for maintaining an organ, tissue or section of anatomy in a near normal metabolic state outside of, or at least isolated from the circulatory system of the body. The system comprises an organ chamber for holding an organ, having means to collect organ product generated during perfusion; a perfusion delivery subsystem comprising one or more perfusion fluid paths for circulating and regenerating a warm perfusion solution capable of supporting the organ in a near normal metabolic state; a controlled gassing subsystem for regulation of respiratory gases and pH of the perfusate; a temperature controller for controlling temperature of the perfusate; and a monitoring subsystem for monitoring various parameters of the perfusate.

In a related aspect, the invention relates to a monitoring subsystem in which the monitoring of various parameters of the perfusion solution is computer controlled. Such a system would include a computer, and sensor means interposed in the perfusate flow path, and coupled to the computer for sensing at least one of the temperature, pH, pressure, flow rate, $PaO_2$, $PaCO_2$, and osmolarity of the perfusion solution and providing the sensed information to the computer.

In another aspect, the invention relates to a method for the maintenance of an organ or tissue for transplantation, comprising the steps of flushing the organ with a buffered physiological solution to remove blood and blood products, establishing and maintaining the organ in the exsanguinous metabolic support system of the present invention, and monitoring the functional integrity of the organ.

In yet another aspect, the invention relates to a method for the effective delivery of an exogenous molecule to a target tissue comprising the steps of removing a target tissue or organ from a living body, flushing the organ with a buffered physiological solution to remove blood and blood products having accumulated in the organ during isolation of the organ, maintaining the target tissue in a recirculating, oxygenated perfusion solution, in a near normal metabolic state at 25–37° C.; contacting the target tissue with the exogenous molecule to be delivered in the perfusion solution, and then returning the organ or tissue to the body of the donor or another recipient. Where there has been any form of insult or injury which compromises the functional integrity of the organ, for example, where a period of more than 30 minutes since cessation of blood flow to the organ has occurred, it is desirable to monitor the function of the organ prior to exposure to the therapeutic agent to be delivered to evaluate the functional integrity of the organ and determine whether there has been irreparable damage to the tissue which will affect the ability of the organ to function normally posttransplantation.

In a related aspect, the invention relates to a method for the effective delivery of an exogenous molecule to a target tissue comprising the steps of isolating a target tissue or organ from the rest of the circulatory system of a living body, flushing the organ with a buffered physiological solution to remove blood and blood components, maintaining the target tissue in a recirculating, oxygenated perfusion solution, in a near normal metabolic state at 25–37° C., contacting the target tissue with the exogenous molecule to be delivered in the perfusion solution of the invention for a period of time sufficient to effectuate delivery of the molecule and then returning the organ or tissue to the rest of the circulatory system of the body.

In yet another aspect, the invention relates to a solution to be in employed in an exsanguinous metabolic support system comprising a buffered basal medium which contains essential and non-essential amino acids, carbohydrates, metabolites, inorganic ions, serum proteins, lipids, hormones, nitrogen bases, vitamins, reducing agents and a buffering system and additional components for oxidative metabolism including coenzyme A, FAD, DPN, Cocarboxylase, TPN, 2'-deoxyadenosine, 2'deoxyguanosine, 2'-deoxycytidine, thymidine, adenosine, guanosine, cytidine, uridine, ATP, AMP, and UTP.

In still another aspect, the invention relates to a method for storing a tissue, explant or organ intended for transplantation comprising the steps of flushing the tissue, explant or organ with a non-blood buffered physiological solution to remove blood and blood products; perfusing the tissue, explant or organ in a warm preservation system capable of maintaining the tissue, explant or organ at a near normal rate of metabolism for a period of time sufficient to impart protection to the tissue, explant or organ; and storing the organ at 4–8° C.

DETAILED DESCRIPTION OF THE INVENTION

Figure 1:
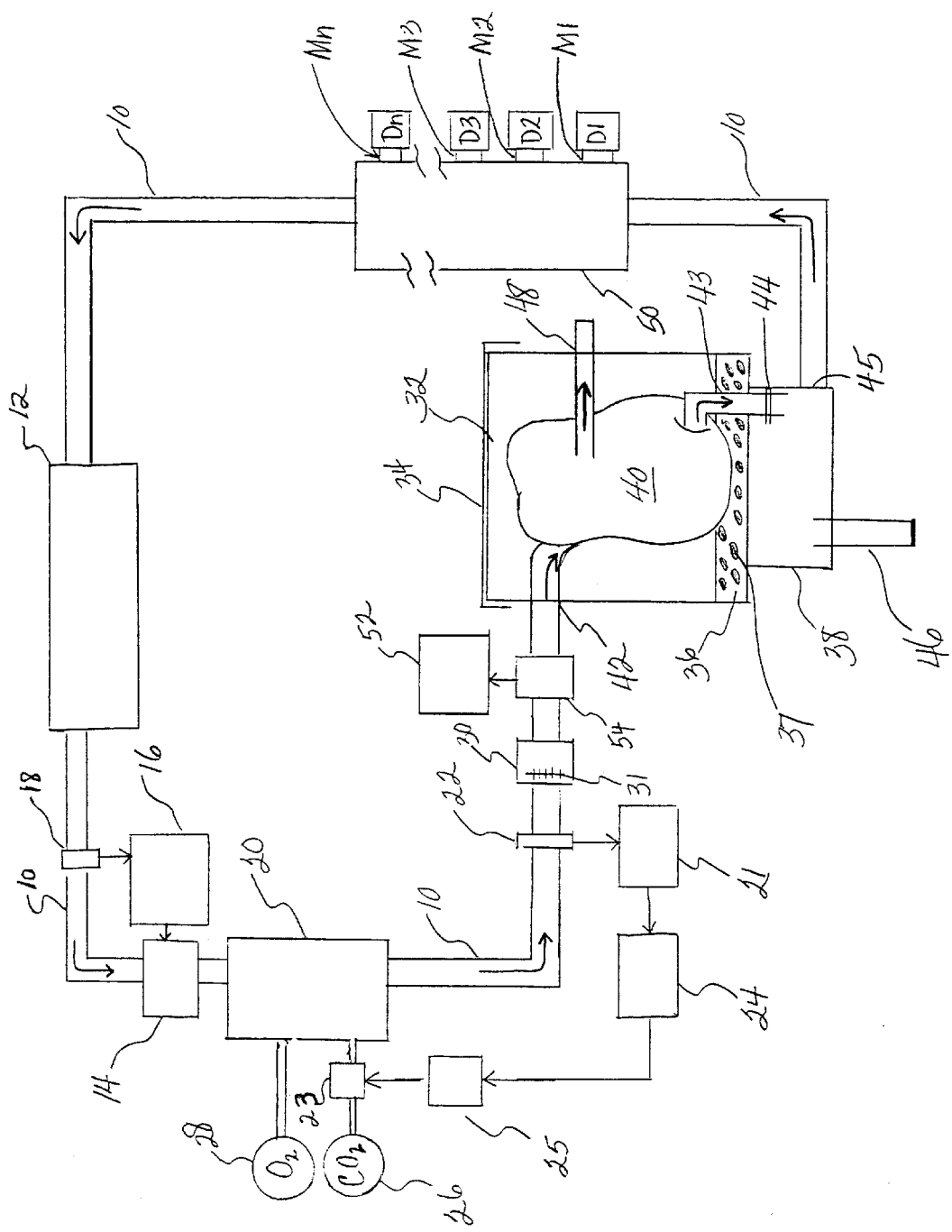
FIG. 1 shows an embodiment having a closed loop perfusion subsystem for circulating the perfusion fluid and a dialysis subsystem for reprocessing it.

All literature references, patent applications, and patents cited herein, including U.S. Pat. Nos. 6,024,698, 5,843,024, 5,699,793 and 5,599,659 are hereby incorporated by reference in their entirety into the subject application.

Numerous perfusion apparatus are described elsewhere, for example, those disclosed in U.S. Pat. Nos. 5,856,081; 5,716,378; 5,362,622; 5,356,771; 5,326,706; 4,186,565 and 3,995,444. None, however, employs a warm preservation solution and is able to support and control ongoing organ metabolism and resulting function of an organ intended for transplantation. In order to do so, the organ's physical processes must be maintained and controlled by a metabolic support system (EMS) such as the one described herein. The EMS perfusion system of the present invention delivers a warm perfusion solution containing all the constituents necessary to reestablish, where necessary, and support oxidative metabolism by the organ. The perfusion system may also reprocess the perfusion solution to ensure a continuous supply of nutrients and chemical energy substrates and remove metabolic by-products. Additionally, the EMS monitors and controls various parameters of the perfusion including temperature, vascular pressures, perfusion flow rate, OsM, pH, $PaO_2$, $PaCO_2$, nutrient delivery and the removal of waste products.

In the description that follows, certain conventions will be followed as regards the usage of terminology: The term "organ, tissue or section of anatomy" refers to an excised viable and whole section of the body to be maintained as such in the EMS of this invention, and refers to an intact organ including, but not limited to, a kidney, heart, liver, lung, small bowel, pancreas, brain, eye, skin, limb or anatomic quadrant. The term "organ product" refers to any substance generated as the result of the secretory function of an organ, frequently a fluid, for example, bile from liver, urine from kidneys, but also includes mechanical functions such as kidney filtration or heart pumping.

The terms "perfusion solution" and "perfusate" are used interchangably and refer to a non-blood buffered physiologic solution that provides means for reestablishing cellular integrity and function in organs which may have experienced ischemic damage prior to or during isolation and further, enables an organ or tissue to be maintained at a near normal rate of metabolism. The term "non-blood" is intended to exclude perfusates comprising substantially whole blood or its individual components. The perfusion solution of the present invention may, however, contain a minimal amount of whole blood or a blood component, for example, red blood cells, serum or plasma.

The terms "near normal rate of metabolism" and "near normal metabolic rate" are defined as about 70–100% of the normal rate of metabolism for a particular organ as determined by measuring and evaluating whether functional characteristics of an organ, such as those described in U.S. Pat. No. 5,699,793, are within the range associated with normal function for that particular organ. Examples of functional characteristics include, but are not limited to, electrical activity in a heart as measured by electrocardiogram; physical and chemical parameters of organ product, for example, oxygen consumption and glucose utilization which can be ascertained from perfusate concentrations; pancreatic enzymes; heart enzymes; creatinine clearance and filtration functions, and specific gravity of urine and so on.

The term "therapeutic agent" refers to any molecule used to effect a functional, metabolic, immunogenic or genomic change in an organ or tissue. These include but are not limited to viral vectors, liposomes, episomes, naked DNA, either sense or anti-sense molecules, RNA, chemotherapeutic agents, biologics, such as cyokines and chemokines and the like.

The process according to the present invention involves isolating an organ, tissue or specific area of anatomy from the rest of the physiologic system by removing or interrupting the arterial source of blood feeding the desired tissue(s). Likewise, the venous outflow from the organ or section of anatomy is interrupted and the venous effluent is collected. If the tissue is completely excised from the body, then the enervation and lymphatics of the tissue(s) are also isolated. Next, the organ or tissue is flushed through the arterial system with the solution of the present invention at a temperature of about 25°–37° C. to remove blood and blood products. The organ is then placed in the exsanguinous metabolic support system of the invention and perfused with the solution of the present invention, while various parameters of the perfusion are monitored by the system and regulated as necessary to maintain adequate metabolism of the organ or tissue. Organ function, is also monitored, for example, by collecting an organ product, such as urine or bile, and evaluating whether physical and chemical parameters of the organ product are within the range associated with normal function for that particular organ. The invention may optionally include, therefore, a subsystem for evaluating the functional status of the organ. In this way, organ function can be monitored using in-line detection means and in-line testing methodology.

Perfusion of the isolated organ or section of anatomy with a solution at near physiologic temperature of about 25° C. to 37° C., in accordance with the invention, performs a number of functions. It maintains the cellular environment at physiologic pH and maintains near normal oxygenation, temperature, and osmolarity. It maintains the normal barrier function of the tissue to macromolecules, thereby resulting in stable perfusion pressures and stable vasculature flow rates. It adequately dilates and fills the vasculature, delivers adequate trophic factors to maintain a near normal level of metabolism in the isolated organ or section of anatomy and supports the artificially interrupted aerobic metabolism by providing high energy compounds. It supports ongoing oxidative metabolism with supplemental substrates that may include, but are not limited to, glucose, pyruvate, and uridine 5-triphosphate (UTP). The ongoing oxidative metabolism is further supported by maintaining the adenine compound pool. The citric acid cycle and the electron transport chain are supported by providing adequate substrate delivery to continue metabolic support and function in the isolated organ and tissues. The ongoing metabolism supported by the method and solution of the invention provides adequate metabolites and nutrients to maintain the tissue integrity with tight cellular functions and normal membrane polarity.

The method and system of the invention allows for the removal of blood within the organ or section of anatomy and refills the vascular and pericellular spaces with the solution of this invention. Further, the system maintains pH, $PaO_2$, temperature, osmolarity, and hydrostatic pressures and delivers adequate substrate to support the metabolism necessary for cellular integrity. The ongoing metabolism provided by the method, solution and system, in combination, is of sufficient level to support the ongoing function of the specific organ or section of anatomy during the time the tissue(s) are isolated from the body or the circulatory system.

For purposes of illustration, and not limitation, the solution is perfused at a systolic pressure appropriate for the tissue(s) being maintained with the EMS organ culture technology of this invention until a flow rate is achieved which is near normal for that particular organ or tissue. By way of illustration but not limitation, a human kidney may be perfused with the solution at a systolic pressure of <80 mmHg with a flow rate >80 cc/min. The pH is maintained in a physiologic range by the injection of $CO_2$ or $O_2$ via an oxygenator. Adequate oxygen is provided to the organ by including an oxygen transporting compound as a component of the solution.

The method, solution and system according to the present invention provides the necessary oxygen delivery, nutrients for metabolism, oncotic pressure, pH, perfusion pressures, temperature, and flow rates to support adequate organ metabolism near the respective physiologic range. A near normal rate of metabolism as defined above is about 70–100% of normal rates of metabolism. Further, the method, solution and system according to the present invention supports a level of metabolism during the period of EMS organ culture which supports sufficient oxidative metabolism to result in the normal functional product of the organ or section of anatomy.

The exsanguinous metabolic support (EMS) technology of the present invention provides, therefore, a number of advantages over conventional cold preservation methodologies: (1) Organs intended for transplantation can be maintained in a metabolically active state for a prolonged period of time prior to being transplanted during which the functional integrity of the organ can be assessed and the likelihood of its ability to function posttransplantation can be evaluated. (2) Organs which were previously thought to be unsuitable for transplantation due to excess periods of warm ischemia can be resuscitated and repaired; (3) EMS perfusion prior to exposure to cold ischemia in traditional cold storage protocols provides tissue protection and allows for extended periods of cold storage of an allograft as compared to immediate cold storage following harvest of the organ; (4) EMS perfusion provides means for targeted delivery of a therapeutic agent, for example, in chemotherapy or gene therapy.

Perfusion Solution

Organ preservation and perfusate solutions are known in the art as comprising a base solution that consists of a buffered physiological solution, such as a salt solution or a cell culture-like basal medium, to which is added a variety of defined supplements. The perfusion solution of the present invention employs such a base solution containing amino acids in quantities sufficient to support protein synthesis by the metabolizing organ, ions, physiologic salts, serum proteins, carbohydrates, and a buffering system for maintaining pH at physiologic levels. Furthermore, the perfusion solution of the present invention has been designed to support the nutritional and metabolic needs of the vascular endothelium within a graft, thereby maintaining the integrity of the vasculature and, subsequently, the normal permeability of the organ.

The buffered basal medium may be any commercially available salt solution or cell culture medium, (e.g., Hank's BSS, Earle's BSS, Ham's F12, DMEM, Iscove's, MEM, M199, RPMI 1640, RSM-210.) In one embodiment of the perfusion solution of the present invention, a bicarbonate buffer system is employed. The bicarbonate buffer works in concert with the respiratory gas controller subsystem of the EMS system to automatically maintain the pH of the perfusion solution in a narrow range, 7.0 to 7.6, and more preferably, 7.30–7.45, which approximates respiratory control of blood pH by the lungs.

To the basal medium are added a number of supplements, including, but not limited to, essential and non-essential amino acids, growth factors, vasodilators, vitamins, and chemical energy substrates, in a physiologially effective amount to support oxidative metabolism by the organ or tissue.

Amino acids to be included in the perfusion solution of the present invention include the basic set of 20 amino acids and may be D- or L-amino acids, or a combination thereof, or may be modified amino acids, such as citrulline, ornithine, homocysteine, homoserine, β-alanine, aminocaproic acid and the like, or a combination thereof.

Chemical energy substrates added to the perfusion solution may include pyruvate, glucose, ATP, AMP, coenzyme A, flavin adenine dinucleotide (FAD), thiamine pyrophosphate chloride (cocarboxylase), β-nicotinamide adenine dinucleotide (DPN), P-nicotinamide adenine dinucleotide phosphate (TPN), uridine 5' triphosphate (UTP) chloride. The chemical energy substrates comprise from about 0.01% to about 90% by volume of the combination of supplements added to the base solution in preparing the perfusion solution of the present invention.

Also added to the basal medium are nucleic acids for DNA repair and synthesis including 2' deoxyadenosine, 2'deoxyguanosine, 2'deoxycytidine, adenosine, thymidine, guanosine, cytidine and uridine. The solution of the present invention may further comprise hormones, such as insulin, and thyroid stimulating hormone (TSH) and growth factors (GF), such as platelet-derived growth factor (PDGF), fibroblast growth factor (FGF-1, FGF-2), insulin-like GF I and II, epithelial GF, epidermal GF, brain-derived FGF, somatomedins A1, A2, B and C, nerve growth factor (NGF), vascular endothelial growth factor (VEGF), heparin-binding growth factor (HBGF), endothelial cell growth factor (ECGF), transforming growth factor (TGF), glucocorticoids and urogastone. Also included are cytokines such as IL-1, colony stimulating factor (CSF), and erythropoietin.

The perfusion solution of the present invention also comprises serum albumin and/or mucopolysaccharides such as chondroitin sulfate B, heparin, petastarch, hetastarch, and plasma expanders as a source of colloid, and lipids, such as linoleic acid, arachidonic acid, linolenic acid, eicosapentaenoic acid, docosahexaenoic acid, oils. Additionally, attachment factors, antioxidants, vasodilators and impermeants maybe included in the perfusion solution of the present invention.

The high osmolar solution of the present invention is used for the initial organ flushing, and as a perfusate for long term maintenance of an organ in the EMS system using warm preservation technology (18°–35° C.) without extreme hypothermia. The solution has been designed to support the nutritional and metabolic needs of the vascular endothelium within a graft, thereby maintaining the integrity of the vasculature and subsequently the normal permeability of the organ. While some of the components of the solution of the present invention are similar to those of other known tissue culture media, and of other known preservation solutions for organ transplantation with extreme hypothermia, the solution of the present invention was specifically designed to potentiate the simultaneous growth of microvessel and large vessel endothelial cells, to support the integrity of vascular endothelium within a graft; and to support normal permeability and metabolism without extreme hypothermia. The enhanced ability of the solution to serve as a preservation solution for organs for transplantation using a warm preservation technology, may be attributed to supplementation with serum albumin as a source of protein and colloid, vasodilators to ensure adequate dilation of the vasculature, trace elements to potentiate viability and cellular function, pyruvate and adenosine for oxidative phosphorylation support; transferrin as an attachment factor; insulin and sugars for metabolic support; and glutathione to scavenge toxic free radicals as well as a source of impermeant; cyclodextrin as a source of impermeant, scavenger and potentiator of cell attachment and growth factors; a high Mg concentration for microvessel metabolism support; mucopolysaccharides, comprising primarily chondroitin sulfates and heparin sulfates, for growth factor potentiation and hemostasis; and ENDO GRO™ as a source of colloid, impermeant and growth promoter. As a result, the preservation solution of the present invention has been found to preserve organs without extreme hypothermia, and does not present the common problems encountered with cold perfusates, namely, edema, vasospasm, depletion of ATP stores, shutdown of ion pumps, glycolysis, and the generation of cold-induced toxic free radical intermediates. The preservation solution of the present invention provides for more efficacious preservation thereby presenting the potential to utilize an expanded donor pool, namely, the non-heart beating cadaver donors.

It will be appreciated by those skilled in the art that other components may be substituted for a functionally equivalent compound to achieve the same result. For purposes of illustration, and not limitation, Table I lists components of one embodiment of the perfusion solution of the present invention.

TABLE 1

| | |
|---|---|
| DL-Alanine | 0.12 g/L |
| L-Arginine HCl | 0.14 g/L |
| DL-Aspartic Acid | 0.12 g/L |
| L-Cysteine HCL · $H_2O$ | 0.022 g/L |
| L-Cystine 2HCl | 0.052 g/L |
| DL-Glutamic Acid | 0.2672 g/L |
| L-Glutamine | 0.2 g/L |
| Glycine | 0.1 g/L |
| L-Histidine HCl · $H_2O$ | 0.04376 g/L |
| L-Hydroxyproline | 0.02 g/L |
| DL-Isoleucine | 0.08 g/L |
| DL-Leucine | 0.24 g/L |
| L-Lysine HCl | 0.14 g/L |
| DL-Methionine | 0.06 g/L |
| DL-Phenylalanine | 0.10 g/L |
| L-Proline | 0.08 g/L |
| DL-Serine | 0.10 g/L |
| DL-Threonine | 0.12 g/L |
| DL-Tryptophan | 0.04 g/L |
| L-Tyrosine · 2Na | 0.11532 g/L |
| DL-Valine | 0.10 g/L |
| Adenine Hemisulfate | 0.02 g/L |
| Adenosine Triphosphate · 2Na | 0.002 g/L |
| Adenylic Acid | 0.0004 g/L |
| Alpha Tocopherol Phosphate · 2Na | 0.00002 g/L |
| Ascorbic Acid | 0.0001 g/L |
| D-Biotin | 0.00002 g/L |
| Calciferol | 0.0002 g/L |
| Cholesterol | 0.0024 g/L |
| Choline Chloride | 0.001 g/L |
| Deoxyribose | 0.001 g/L |
| Folic Acid | 0.00002 g/L |
| Glutathione (Reduced) | 0.0001 g/L |
| Guanine HCl | 0.0006 g/L |
| Hypoxanthine | 0.0006 g/L |
| Menadione (Na bisulfite) | 0.00003 g/L |
| Myo-Inositol | 0.00011 g/L |
| Niacinamide | 0.00005 g/L |
| Nicotinic Acid | 0.00005 g/L |
| PABA | 0.0001 g/L |

TABLE 1-continued

| | |
|---|---|
| D-Pantothenic Acid Ca | 0.00002 g/L |
| Polyoxyethylenesorbitan Monoleate | 0.04 g/L |
| Pyridoxal HCl | 0.00005 g/L |
| Pyridoxine HCl | 0.00005 g/L |
| Retinol Acetate | 0.00028 g/L |
| Riboflavin | 0.00002 g/L |
| Ribose | 0.001 g/L |
| Thiamine HCl | 0.00002 g/L |
| Thymine | 0.0006 g/L |
| Uracil | 0.0006 g/L |
| Xanthine Na | 0.00069 g/L |
| Calcium Chloride · $2H_2O$ | 0.265 g/L |
| Ferric Nitrate · $9H_2O$ | 0.00144 g/L |
| Magnesium sulfate (anhydrous) | 1.20 g/L |
| Potassium chloride | 0.4 g/L |
| Sodium Acetate (anhydrous) | 0.1 g/L |
| Sodium Chloride | 6.8 g/L |
| Sodium Phosphate Monobasic (anhydrous) | 0.244 g/L |
| Glucose | 2.0 g/L |
| Insulin | 0.01 g/L |
| Serum albumin | 30.0 g/L |
| $NaHCO_3$ | 4.4 g/L |
| Pyruvate | 0.22 g/L |
| Transferrin | 0.1 g/L |
| Serum | 100 ml |
| Impermeant (cyclodextrin) | 0.5 g/L |
| Mucopolysaccharide (chondroitin sulfate B) | 0.004 g/L |
| ENDO GRO ™ (growth factor) | 0.20 g/L |
| heparin | 0.18 g/L |
| chemically modified hemaglobin* or | 216 mg/L |
| perfluorochemical emulsion* | 20% (v/v) |
| Coenzyme A | 0.010 g/L |
| FAD | 0.004 g/L |
| DPN | 0.028 g/L |
| Cocarboxylase | 0.004 g/L |
| TPN | 0.004 g/L |
| 2'deoxyadenosine | 0.042 g/L |
| 2'deoxyguanosine | 0.042 g/L |
| 2'deoxycytidine | 0.042 g/L |
| thymidine | 0.042 g/L |
| adenosine | 0.042 g/L |
| guanosine | 0.042 g/L |
| cytidine | 0.042 g/L |
| uridine | 0.042 g/L |
| ATP | 0.002 g/L |
| AMP | 0.002 g/L |
| UTP | 0.004 g/L |

*as an oxygen carrier

The perfusion solution contains one or more oxygen transporting compounds ("oxygen carrying agents") that function to provide molecular oxygen for oxidative metabolism to the organ. Such oxygen carrying agents are well known to those skilled in the art and include, but are not limited to, hemoglobin, stabilized hemoglobin derivatives (made from hemolyzed human erythrocytes such as pyridoxylated hemoglobin), polyoxethylene conjugates (PHP), recombinant hemoglobin products, perfluorochemical (PFC) emulsions and/or perfluorochemical microbubbles (collectively referred to as "perfluorochemical"). One such oxygen carrier is a perfluorochemical such as perflubron emulsion (perfluoroocytl bromide, PFOB). Other perfluorochemical emulsions said to be useful as oxygen carrying agents are described, for example, in U.S. Pat. Nos. 5,403, 575; 4,868,318; 4,866,096; 4,865,836; 4,686,024; 4,534, 978; 4,443,480; 4,423,077; 4,252,827; 4,187,252; 4,186, 253; 4,110,474; and 3,962,439. Such liquid PFC emulsions include, but are not limited to perfluorooctyl bromide, perfluorooctyl dibromide, bromofluorocarbons, perfluoroethers, Fluosol DA™, F-44E, 1,2-bisperfluorobutyl-ethylene, F-4-methyl octahydroquinolidizine, 9 to 12 carbon perfluoro amines, perfluorodecalin, perfluoroindane, perfluorotrimethyl 1599.005A bicycle [3,3,1] inane, perfluoromethyl adamante, perfluorodimethyl adamantine. Such oxygen carrying agents comprise from about 0% to about 59% by volume of the supplements which are added to, and dissolved in, the base solution in preparing the perfusion solution of the present invention; or about 0% to about 20% of the total perfusion solution (v/v).

Alternatively, red blood cells (RBC) may be used as an oxygen carrier in an effective amount to support metabolism by the organ being perfused (about 0.1% to 5%.) Generally, about 5 cc of RBC per 500 ml of perfusion solution (that is, about 1%) is an effective amount. When compared to perfluorochemical emulsion or conjugated hemoglobin, RBC provides oxygen concentrations equivalent to the oxygen consumption by the metabolizing organ. This generally occurs at the rate of 0.1–0.3 cc/min/gm. Additionally, after 24 to 48 hours of perfusion, there was no evidence that the RBC were cretinated. Therefore, an amount of RBC in this range does not present the problem of mechanical damage to the organ associated with blood-based perfusates.

RBC (5 cc per 500 ml of perfusate) were added to the circulating perfusate until a $PaO_2$ of >200 mmHg was obtained. Stable perfusion pressures, vascular flow rates and diuresis were achieved (See Table 2).

| Oxygen Carrier-RBC* | | | |
|---|---|---|---|
| Oxygen Consumption | Perfusion Pressure | Flow Rate | Urine Flow |
| 0.25 cc/min/gm (+/−0.04) | 48 mmHg(+/−1.0) | 98 cc/min(+/−5.0) | 0.5 cc/hr/gm (+/−0.001) |

*expressed as the mean from 5 experiments collected over a 10 hour perfusion period

| Urine Evaluation** | | | |
|---|---|---|---|
| | BUN | Total Protein | Creatinine |
| urine | 24.6 mg/dL | 0.00 gm/dL | 19.14 mg/dL |
| perfusate | 3.5 mg/dL | 3.50 gm/dL | 4.33 mg/dL |

**expressed as the mean from the 5 experiments collected over 10 hours of perfusion The perfusion solution of the present invention may additionally comprise vasodilators, in a physiologically effective amount which provide a means to adequately dilate large vessels via smooth muscle cell relaxation, as well as to adequately dilate microvessels. To insure that normal permeability of the vasculature is maintained, the vasodilation is controlled in an endothelial cell-dependent manner. Vasodilator components for use in the perfusion solution of the present invention include (i) substrates for endothelial cell mediated vasodilation, such as acetylcholine, dopamine, bradykinin, and arginine; (ii) substrates for microvessel vasodilation, such as prostacyclin (and analogs, e.g. carbacyclin) and $Mg^+$; and (iii) adenosine (and analogs, e.g. cyclohexyladenosine), and verapamil for their combined effects on vascular dilation mediated by calcium channel blocking. Other calcium channel blockers encompassed by the invention include flunarizine, nifedipine, SNX-11, chlorpromazine, and diltiazem. Use of the aforementioned vasodilators ensures that the vasculature is well dilated while simultaneously retaining its integrity and normal barrier function. The vasodilators comprise from about 1% to about 50% by volume (w/v) of the combination of supplements which are added to the base solution in preparing the perfusion solution of the present invention.

EMS Perfusion Subsystem

The instant invention is described with reference to a preferred embodiment. It should be understood that the various components of the system may be combined or provided as separate parts which arc implemented in the system as a matter of design choice.

Figure 2:
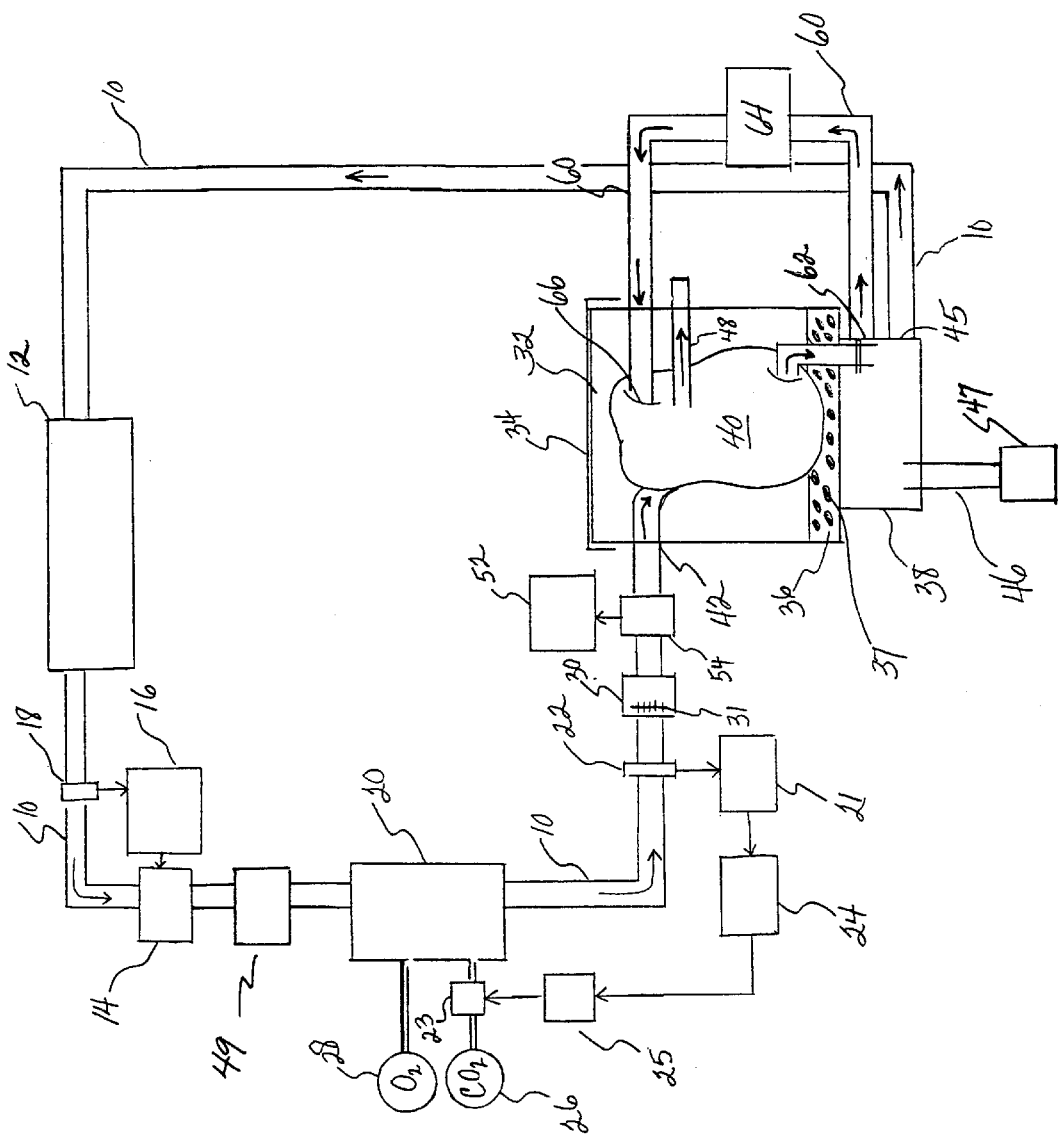
FIG. 2 shows an embodiment, having a perfusion exchange subsystem and two perfusion paths, which is suitable for preservation of a liver.

FIG. 1 is a diagram of one embodiment of the organ perfusion circulation path of the present invention. In most instances, only one perfusion path is necessary. When the organ to be metabolically maintained is a liver, however, two perfusion circuits are required. These are illustrated in FIG. 2 and described in more detail below. All perfusate available for circulation through the system is propelled through the circulation path 10 by a pump 12. The direction of flow of the perfusion solution is indicated by arrows within the flow path. While any pump may be used to circulate the perfusion fluid of the instant invention, a pulsatile pump such as Model No. MOX-100™, (Waters Instruments, Inc., Rochester, Minn.) is preferred.

Before the perfusate enters the organ chamber 32, it passes through a heat exchanger 14, to bring the temperature within the range of 25°–37° C., the preferred temperature for optimal metabolism being in that range. The heat exchanger 14 is controlled by a temperature controller 16 which receives input from a temperature sensor 18 situated in the perfusate path 10. In one embodiment, the temperature controller is a single unit comprising a thermocouple which senses the temperature of the perfusate and a heat exchanger which is activated by the thermocouple, when required, to maintain the temperature in the desired range.

The perfusate, which contains an oxygen carrier, is also oxygenated prior to contact with the organ via a hollow fiber or membrane oxygenator 20, for example, a pediatric size oxygenator, such as those available from Sarnes, to provide a partial pressure of oxygen, in most cases, in the range of 100–240 mmHg. When situated in the perfusion path delivering perfusate to the portal system of the liver, however, the partial pressure is maintained in the range of 80–140 mmHg. In a preferred embodiment, the oxygenator 20 is situated in the perfusion solution flow path 10 between the heat exchanger 14 and pH sensor 22. The oxygetator may be an independent unit or may be combined with another component of the system to form a single unit, for example, combined with the heat exchanger, or as part of the organ chamber.

The pH and $PaCO_2$ of the perfusion solution are controlled by automatic intermittent gassing of the perfusate with $CO_2$ to provide a circulating perfusate having a pH in the range of 7.30–7.45 and a partial pressure of $CO_2$ of 30–60 mmHg. Finally, the perfusate is debubbled in a conventional bubble trap 30 just prior to entering the organ chamber 32. The perfusate leaves the organ as venous effluent and, in one embodiment, drains by gravity directly into an effluent reservoir 38 situated beneath the compartment of the organ chamber 32 which holds the organ. In a preferred embodiment, the effluent is directed to the effluent reservoir 38 by means of tubing 43 which connects to a conventional non-traumatic cannula which has been inserted into he vein of the organ 40.

The specifications of the organ chamber 32 used depend on the organ to be maintained. For example, when the organ is a liver, the organ chamber must have more than one perfusate inlet to accommodate two simultaneously operating perfusion flow paths (FIG. 2). When the organ is a heart, an open vertical tube, extending upward from the perfusate flow path above the point of entry of perfusate into the heart, provides a column of perfusate, such that sufficient pressure is maintained to counter the expulsion of the perfusate by the beating heart. Generally, however, the organ chamber comprises a container 32, adequate in size to accommodate the organ 40 to be maintained, and having a removable cover 34, which is made of a rigid material and has means, such as a translucent panel, for viewing the interior of the chamber. The organ chamber 32 has means 36 for supporting the organ 40 within the chamber 32 and further comprises one or more perfusate inlets 42, means 48 for collecting organ product from the organ 40 and, in one embodiment, a reservoir 38 for the perfusate effluent having an effluent outlet 45. Organ support means 36 may be of a rigid material such as stainless steel, or preferably, of a mesh-like fabric which suspends the organ in a sling-like fashion. The support means 36 may have one or more openings 37 which allow passage of perfusate to the reservoir below. In an alternate embodiment, the organ chamber 32 has one or more effluent outlets which direct the perfusate to a perfusate reservoir which is separate from the organ chamber. The perfusate reservoir 38 of the instant invention additionally comprises means 46 for perfusate exchange. The organ chamber may be a disposable single-use unit or of a suitable material, such as stainless steel, which can be sterilized and reused.

The venous effluent from the organ is collected by gravity flow directly into the reservoir 38 of the organ chamber 32 through openings 37 in the support means 36 or, in a preferred embodiment, by cannulating the vein using a non-traumatic cannula and connecting a length of tubing 43 to conduct the effluent away from the organ. The effluent is filtered through a filter 44 having a pore size of 0.22 microns, such as those available from Millipore Corp., to remove debris and any bacterial contaminants.

Collection of effluent, in this manner, provides the additional benefit of minimizing perfusion contamination due to contact with air. Once the perfusion solution is collected in the effluent reservoir 38, it is regenerated, either by perfusate exchange or by dialysis in the perfusion dialysis subsystem 50 and recirculated through the system.

Perfusion Regeneration

Because of the continuous metabolic utilization by the organ of the constituents of the perfusion solution in the system of the instant invention, the perfusate would eventually be exhausted without some replenishment or regeneration. In one embodiment, the ingredients necessary to support metabolism can be replenished by perfusate exchange, that is, removing a portion of the spent perfusate via means 46 in the reservoir and replacing it with fresh perfusate.

Perfusion Exchange

In one embodiment, the perfusate is exchanged by means of two volume-regulatable pumps 47 and 49; pump 47 is connected to means 46 in the reservoir to extract depleted perfusate, and pump 49 is situated in the perfusate path 10 just prior to the oxygenator 20. Removal of depleted perfusion solution by pump 47 is immediately followed by introduction of an equal volume of fresh perfusate into the system by pump 49. Exchange in this manner can be continuous or intermittent. The rate of exchange is dependent upon temperature and/or metabolic rate of the organ being perfused.

By introducing fresh perfusate into the perfusion path just prior to the oxygenator 20 and pH control system, the PaO2 and pH of the perfusate remain constant. In this way, metabolic by-products are removed and fresh solution is administered to maintain ongoing metabolism by the organ without acidosis developing. Perfusate volume remains constant as does perfusate osmolarity.

Perfusion Dialysis

In some situations, however, replenishment of nutrients necessary to sustain metabolism of the organ by perfusate exchange is inadequate to keep up with the rate of metabolism. In an alternate embodiment, therefore, the perfusate is continuously regenerated by dialysis, alone or in combination with perfusate exchange.

In the dialysis subsystem of the invention, nutrients and chemical energy substrates necessary for continued metabolism are re-introduced into the perfusate by one or more dialyzer units. Such units, singly or in series, allow the supply of nutrients in the perfusate to be replenished, in a manner similar to dialysis for removal of catabolites from perfusate.

The perfusion dialysis subsystem of the EMS, as shown in FIG. 1, comprises an effluent reservoir 50 in fluid communication with the perfusion flow path and one or more nutrient reservoirs D1, D2, D3, Dn. Nutrient reservoirs, D1, D2, D3, Dn, are in communication with the effluent reservoir 50 via semi-permeable membranes M1, M2, M3, Mn of varying molecular weight cut-offs in the range of 1,000–80,000 daltons. These nutrient reservoirs contain concentrated amounts of components necessary to regenerate the perfusion solution, which are allowed to diffuse into perfusate in the effluent reservoir 50.

In one embodiment, where more than one is used, the nutrient reservoirs are arranged in order of decreasing molecular size, so that the perfusate flowing by is contacted first, by the nutrient with the largest molecular size, followed by nutrients with increasingly smaller molecular weight. This ensures that any components which might be lost at the first dialyzer unit are replenished by exposure to subsequent units before leaving the perfusion dialysis system. The system further comprises means for regulating the volume of the perfusion solution, so that an equilibrium is maintained between the effluent reservoir and the nutrient reservoirs.

Monitor and Control System

The perfusion solution monitor subsystem performs a plurality of functions, using standard components and hardware to monitor various parameters of the perfusion solution. Temperature is sensed and controlled by a thermocouple 18 linked to the heat exchanger. One or more manometers 31 situated in the perfusion solution flow path, for example, as a component part of bubbletrap 30, are used to monitor the vascular resistance to the perfusate and the partial pressures of the respiratory gases. A flowmeter 52, for example, an ultrasonic device, such as those available from Transonic, for detecting flow rate having a sensor 54, which clips onto the tubing carrying the perfusate, is used to monitor the flow rate of the perfusate. In a preferred embodiment, the flowmeter is situated in the flow path between the bubble trap and organ chamber. Osmolarity of the perfusate is assessed using the conventional freezing point depression method. Alternatively, osmolarity may be monitored using in-line detection means to assess the concentration of major constituents of the perfusion solution. A sample of perfusate may be removed via the bubbletrap 30 or some other means situated in the perfusion flow path for this determination. It should be understood that a microprocessor and suitable software can also be utilized for control purposes; all are within the skill of the ordinary artisan. Components of the control subsystem may be combined or provided as separate parts which are implemented in the system as a matter of design choice.

Maintenance of pH and Respiratory Gases

The perfusion solution is continuously oxygenated by introducing 100% oxygen 28 via a membrane or hollow fiber oxygenator 20 to maintain a partial pressure of $O_2$ (Pa $O_2$) of 100–250 mmHg. The system of the instant invention includes a novel mechanism for maintaining a perfusate pH between 7.32 and 7.38 and the level of $CO_2$ in the perfusate at a partial pressure of 30–60 mmHg. Regulation of pH and $CO_2$ levels of the perfusate is achieved by the controlled intermittent gassing of the perfusion solution with $CO_2$. The system continuously monitors the pH, for example, by a pH electrode or sensor 22 in the perfusion path 10. The pH sensor 22 is operatively connected to a controller 24 and solenoid 25 for regulation of the $CO_2$ 26 gassing required to maintain tight control of the pH.

In one embodiment, one or more pH meters 21, for example, Model HI 8711 by Hanna Instruments, monitors the pH of the circulating perfusate by way of sensors or electrodes 22 situated in the perfusion flow path 10. An in-line controller 24, such as the Datalogger by Breonics, Inc., receives inputs from the pH sensors 22 via a pH meter 21 connected to the controller 24 and operates a valve interface 23 by way of solenoid to release $CO_2$ 26 into the perfusion solution When the pH rises above 7.35, thereby exceeding the set point of the controller 24, the gassing system is activated by way of valve interface 23 and solenoid 25, and $CO_2$ 26 is injected into the perfusion solution until a pH of 7.35 again is reached, at which point the system is deactivated and the gas is turned off. The intermittent gassing of the perfusion solution with $CO_2$, in this manner, when used in conjunction with a perfusion solution having a bicarbonate buffer system is especially effective in mimicking the tight physiologic control of blood pH by the respiratory system.

Establishing Organ in EMS

In accordance with the invention, once an organ is isolated, a sufficient amount of the perfusion solution is slowly introduced by infusion via a cannula into the major arterial blood supply for the particular organ to be perfused until the effluent is free of blood. It will be appreciated by those skilled in the art that the amount of the perfusion solution sufficient for use in flushing the organ may depend on the particular organ type and size, as well as the length of time the organ was deprived of blood flow. For example, 200 to 600 mls of the perfusion solution may be sufficient to flush a human kidney which has been deprived of blood flow for a period of 1–3 hours. In this way, any ischemic blood and acidotic products which have accumulated in the vascular space are removed. Further, pH is restored and fresh substrate is delivered to support anaerobic metabolism and other cellular pathways necessary for cellular integrity and function.

After flushing, the organ is immobilized within the interior space of the organ chamber, for example, by suspending in a sling-like mesh or by encasing in a gelatinous coating which fills or nearly fills the interior space of the chamber, so as to prevent the organ from moving around in the chamber, particularly during transport. An additional benefit of the coating is that the risk to the organ of contamination by contact with air is minimized. The organ is then connected to the perfusion solution path by a short length of tubing connecting the cannulated artery to an inlet port of the organ chamber. It is desirable that all the tubing used in the instant invention be made of an inert, sterilizable material, for example, silicon or Tygon® tubing.

The organ is perfused, while the perfusion solution is maintained at a temperature in the range of 25° C. to 37° C. At the same time, the system regulates the $PaO_2$, $PaCO_2$. and pH of the perfusate with the gassing subsystem, and monitors the flow rate vascular pressure and osmolarity.

During the perfusion period, the functional integrity of the organ is also monitored. For example, means located on the organ chamber for extracting organ product from the organ during the perfusion period make it possible to monitor organ function by tracking organ output and evaluating physical and chemical parameters of the product of the perfused organ relative to ranges indicative of normal organ function.

The effectiveness of the invention in supporting the organ culture of various organs and tissues was evaluated. The invention was used to establish efficacy with canine kidney, bovine kidney, rat hearts, human placenta and bovine limbs.

EXAMPLE 1

Canine kidneys were isolated, the renal artery was cannulated and the solution was applied with the process and system of the present invention. All blood was removed from the kidneys and the kidneys were perfused with the solution. The kidneys were maintained with the support of the EMS organ culture technology at 32° C. for three days. Similarly, a physiologic pH, osmolarity, pressures, flow rates, and oxygen consumption were maintained during the period of the EMS organ culture. The kidneys remained intact and continued to metabolize during the period of organ culture. The ongoing metabolism in the kidneys remained sufficient to result in continued function, that is, the kidneys continued to produce urine through out the period of the organ culture. The results of the culture of intact whole kidneys is listed in Table 2. There was no deterioration in metabolism or function in any parameter category during the period of the EMS organ culture. Similarly, no edema developed, nor was any necrosis observed following histologic evaluation.

TABLE 2

Organ Culture of Canine Kidneys

| PARAMETER | RESULTS* |
|---|---|
| kidneys | N = 10 |
| $O_2$ | >7.0 cc/min |
| perfusion pressures | 60/30 mmHg |
| flow rates | >100 cc/min |
| weight gain | <10% no edema |
| glucose metabolism | ≧28 mg/hr |
| function | urine production >80 cc/hr |
| histology | normal |

*data represented as the mean from the three days in EMS organ culture

EXAMPLE 2

In order to evaluate species differences, bovine kidneys were also tested. Bovine kidneys were placed in EMS organ culture for three days using the same techniques described in Example 1. Similar to the results using canine kidneys, the bovine kidneys could be maintained in EMS organ culture, intact for three days without loss of ongoing metabolism or resulting function. Similar to the results obtained with canine kidneys, the bovine kidneys exhibited stable perfusion pressures, flow rates and lack of edema during the period of organ culture. Upon histologic evaluation, the bovine kidneys appeared normal, with excellent preservation of all components of the kidney architecture.

EXAMPLE 3

Hearts from rats were excised and the aorta was cannulated. The hearts were placed in EMS organ culture with the present invention and maintained for 24 hours. The results of the testing using the rat hearts are listed in Table 3.

TABLE 3

Rat Hearts in Organ Culture

| PARAMETERS | RESULTS* |
| --- | --- |
| N | 6 |
| perfusion pressure | systolic 50 mmHg |
| flow rate | 30 cc/min |
| edema | <10% wgt gain |
| function | mechanical & electrical |
| histology | normal |

*after 24 hours of EMS organ culture

Following the period of EMS organ culture, three of the hearts were transplanted to evaluate if the hearts were of sufficient integrity to sustain life. All three hearts beat spontaneously, without assistance, and were able to sustain life.

EXAMPLE 4

Human placentas with the umbilical cords still attached were collected. A cannula was placed in the umbilical cord vein and the organ was flushed of its blood with the solution of the present invention. Once the organ was flushed of blood and the vascular compartment was filled with the solution, the organ was placed in EMS organ culture. The organ was maintained intact with the EMS organ culture technology for approximately 22 hours. During the period of organ culture, the flow rate of the solution through the placenta was 92 cc/min with a systolic pressure of 80 mmHg. At the conclusion of the EMS organ culture, the intact placentas were evaluated histologically. Isolated cells were then obtained from both the umbilical cord and the placenta itself. The results are listed in Table 4.

TABLE 4

Organ Culture Results With Human Placenta

| PARAMETERS | RESULTS |
| --- | --- |
| N | 4 |
| histology | normal, all cellular components intact |
| viability: | |
| cord cells | viable cells isolated; 3 passages in tissue culture |
| placenta cells | viable cells isolated; 3 passages in tissue culture |

Viable cells could be isolated from the whole organ following 22 hours in EMS organ culture. Tissue from both the umbilical cord vein and the intact placenta were isolated by collagenase digestion. The cells isolated from the intact organ retained their ability to attach to the culture flask surface and the ability to replicate in standard tissue culture. The isolated cells continued to replicate in standard tissue culture and were eventually passaged three times. Therefore, the intact organ was successfully maintained in the EMS organ culture and was therefore metabolically active. The subsequent viability and function in cells isolated from the whole organ following a period of organ culture supports this interpretation.

EXAMPLE 5

Intact bovine limbs were procured. The femoral arteries were cannulated and the intact limb was flushed of its blood. The solution of the present invention was used to refill the vascular compartment and the limbs were maintained in EMS organ culture for two days. At the completion of the organ culture, the limbs were evaluated histologically. The results of these evaluations indicated the limb cellular components were well preserved without any observed necrosis. Cells isolated from the intact limb following two days in EMS organ culture were likewise viable. The cells isolated from the intact limbs attached to the flask surface in standard tissue culture. The cells continued to proliferate and were passaged three times. Similar to the results obtained with whole organs, sections of anatomy such as the intact limbs could be maintained in he EMS organ culture technology of the present invention.

EXAMPLE 6

The EMS organ culture technology of the present invention was used to maintain human umbilical cords measuring approximately 2–2.5 feet in length. The human umbilical cords were maintained intact in EMS organ culture for at least seven days. The umbilical cord vein was cannulated on one end. On the other end, the vein and the two arteries were connected with silicon tubing connected to a y-connector to form a closed circuit. At the completion of the EMS organ culture, the luminal surface of the umbilical cord blood vessels were digested with collagenase. The isolated endothelial cells were viable and attached to the flask surface in standard tissue culture. The isolated cells demonstrated normal characteristics of endothelial cells in tissue culture; i.e. they attached, replicated and expressed factor VIII antigen. These results demonstrate that the EMS organ culture technology of the present invention can be used to maintain 2–2.5 foot lengths of human tissue intact in EMS organ culture for seven days without loss of viability of the cells within the tissue. These studies demonstrate the efficacy of EMS organ culture technology in maintaining intact organs or large sections of anatomy for extended periods of time.

The EMS whole organ culture technology of the present invention can be used for in vivo applications. A specific organ can be isolated via isolation of the major arterial source feeding the organ and simultaneous isolation and collection of the venous outflow. An in vivo application of the organ culture technology entails physiologic maintenance of the enervation and lymphatic systems. The artery feeding the targeted organ or section of anatomy is cannulated, the vein receiving the organ effluent is likewise cannulated, and blood is flushed from within the tissues. The vascular compartment is refilled with the solution of the present invention. The organ or section of anatomy is maintained in vivo but is "off-line" from the physiologic system and is maintained by the EMS organ culture technology.

EXAMPLE 7

Canine kidneys were isolated by cannulating the renal arteries and veins, flushing the kidneys of blood and refilling with the solution of the present invention. The kidneys were maintained in situ at 37° C. with the EMS organ culture technology for 8 hours. During the isolated, in vivo EMS organ culture, the kidneys continued to metabolize as determined by oxygen and glucose consumption calculations. Likewise, the metabolism was of sufficient levels to result in continuous diuresis. The kidneys, while isolated from the rest of the vascular system and maintained with EMS organ culture technology, continued to produce urine and fill the connected bladder. Upon termination of the EMS organ culture, the cannulas were removed and the kidneys reperfused with blood. The kidneys continued to function normally. All 10 canines demonstrated normal serum chemistries following EMS organ culture of the kidneys.

EXAMPLE 8

Isolated organ or regionalized tissue perfusion is well suited for high-dose chemotherapy delivery while attempting to reduce whole body toxicity. Recent attempts at several cancer institutes to perform isolated organ perfusion to deliver chemotherapeutic agents have carried a high risk of causing damage to non-target tissues. Target organs can be maintained with the organ culture technology of the present invention, without causing any damage. The advantage of using the organ culture technology to deliver chemotherapy is the opportunity to deliver much higher doses while simultaneously reducing or even eliminating the usual systemic side-effects.

The efficacy of the EMS organ culture as a drug delivery technology was established with nontransplantable human kidneys. The kidneys were nontransplantable because of renal tumors identified as renal cell carcinoma. The human kidneys demonstrated stable perfusion pressures, vascular flow rates and oxidative metabolism during the EMS perfusion. Similarly, the human kidneys also consumed oxygen and glucose, produced urine and cleared creatinine. Biopsies of the kidneys were taken both pre- and post-EMS whole organ culture perfusion for histologic evaluations. There were no observed histologic changes following 18 hours of EMS organ culture. Therefore, the EMS organ culture maintains kidneys with renal cell carcinoma without causing damage, thereby providing a delivery system for targeted drug therapies.

EXAMPLE 9

Ischemic insult secondary to occlusive disease such as heart attack and stroke represents another in vivo application of the EMS organ culture technology. Recently developed thrombolytic agents hold great promise for patients suffering a stroke or heart attack. Yet the efficacy of these therapies is dependent upon being able to administer the drugs within a short period of time following the occlusive phenomenon. The tissues downstream from the obstruction are deprived of blood resulting in ischemic damage. The EMS organ culture technology can be used to reperfuse and maintain the tissue downstream from an obstruction, thereby providing an expanded window of opportunity to implement thrombolytic therapies.

The major problems in resuscitation following a major trauma are adequate nutrient delivery and volume replacement. Hemorrhage with subsequent sepsis and multiple organ failure accounts for approximately 60% of the deaths in surgical intensive care units. EMS organ culture technology of the present invention can be implemented to sustain tissue integrity and function in vivo in the resuscitation from shock. Normovolemia can be restored with the acellular solution of the present invention at physiologic temperatures, thereby minimizing the development of a secondary reperfusion injury in patients experiencing a life-threatening hemorrhage. The EMS organ culture technology maintains isolated organs or may be used to maintain the whole patient.

EXAMPLE 10

The addition of appropriate growth factors and hormones to the perfusion solution of the present invention supports cellular repair processes in damaged organs. Kidneys experiencing 60–120 min of warm ischemia were maintained in the EMS whole organ culture technology of the present invention. Following 6–8 hours of organ culture with the organ culture technology of the present invention, mitotic figures were observed in the distal tubules of the thick ascending limb of the loop of Henle. There was no evidence of reparative procedure in the areas in the kidney without apparent damage, i.e., the proximal tubules and glomeruli. These studies demonstrate the substantial potential of the EMS organ culture technology in the repair and regeneration of damaged tissues.

Kidneys removed two hours postmortem were resuscitated and repaired during EMS perfusion as follows. The initial perfusion pressures and vascular flow rates were severely abnormal, with mean perfusion pressures of 24/20 mmHg and the mean vascular flow rate of 4 cc/min/gm. Likewise, the initial oxygen consumption was also impaired with mean values of 0.08 cc/min/gm. The initial assessment of these organs predicted primary nonfunction (PNF) or non-viability.

During 8 hours of EMS perfusion using the process and solutions described herein, the kidneys were repaired. Perfusion pressures and vascular flow rates normalized, oxygen consumption increased to a mean of 0.22 cc/min/gm and urine flow was reinstituted: Normalization of these parameters indicated that the kidneys were resuscitated and repaired sufficiently to change the outcome from PNF to that of viable organs with moderate acute tubular necrosis. Two of these kidneys were transplanted following the determination of viability following 8 hours of EMS perfusion. The third kidney was reimplanted following 18 hours of EMS perfusion. The outcomes listed in the Table 5 below demonstrate not only the viability of the organs, but also demonstrate the role of the EMS technology in the resuscitation and repair of damage from two hours of postmortem warm ischemia.

TABLE 5

| | Serum Creatinine mg/dL/Day Posttransplant | | |
| --- | --- | --- | --- |
| | 8 Hour | | 18 Hour |
| Day | Dog 1 | Dog 2 | Dog 3 |
| 1 | 3.0 | 3.5 | 1.9 |
| 2 | 3.7 | 5.6 | 2.2 |
| 3 | 4.5 | 5.9 | 1.7 |
| 4 | 5.2 | 6.5 | 1.6 |
| 5 | 5.1 | 5.8 | 1.3 |
| 6 | 4.7 | 4.9 | 1.3 |
| 7 | 4.5 | 4.4 | 1.3 |
| 8 | 4.2 | 3.7 | 1.1 |
| 9 | 3.5 | 3.2 | 1.1 |
| 10 | 2.9 | 2.7 | 1.1 |
| 11 | 2.1 | 2.4 | 1.1 |
| 12 | 1.8 | 2.0 | 1.1 |
| 13 | 1.5 | 1.7 | 1.1 |
| 14 | 1.2 | 1.5 | 1.1 |

EMS technology can resuscitate and repair organs from an ischemic insult that today in clinical transplantation is considered to be irreparable damage. The period of EMS perfusion directly correlates with the degree of repair, in that the longer a kidney is perfused the more repaired it becomes. Eight hours of EMS perfusion repaired PNF kidneys sufficiently to become transplantable with peak serum creatinine values on the fourth posttransplant day and normalization on day 12 & 13. Eighteen hours of EMS perfusion provided additional repair that resulted in a slight elevation in serum creatinine value, peaking on day 2 and was normal on the third posttransplant day; more than a week sooner than the kidneys perfused for 8 hours prior to reimplantation.

EXAMPLE 11

The effectiveness of the EMS organ culture technology to preserve livers at near physiologic temperature and the ability to resuscitate liver function following 60 minutes of postmortem warm ischemia (WI) was examined. Measurement of selected parameters indicative of liver viability and metabolic function were made, including oxygen consumption, and standard liver enzymes indicative of acute damage. Metabolic function assessment included measurement of bile production and evaluation of the concentration of enzymes and bilirubin in the bile.

The liver perfusion system described in FIG. 2 differs from the kidney and heart system because of the need to support both the arterial and venous vascular systems. The system described in this invention is unique in delivering a high $PaO_2$,(100–240 mmHg) via the hepatic artery with a lower vascular flow rate (<250 cc/min) and simultaneously providing a low $PaO_2$, (140 mmHg) and correspondingly high vascular flow rate (>240 cc/min) via the portal system. The net effect is to provide a more physiologic perfusion, such that the binary tree is protected and bile production during perfusion is maximized.

As shown in FIG. 2, the effluent reservoir 38, has a second effluent outlet 62 which allows perfusate to be drawn by means of a pump 64, into a second perfusion path 60 carrying perfusate to the portal vein 66 of the liver. Similar to the kidney, the EMS system controls the temperature, perfusion pressure, vascular flow rate, osmolarity, pH, $PaO_2$, $PaCO_2$, nutrient delivery and the removal of waste by-products of the perfusion. This may be done by monitoring and controlling perfusate parameters in the two flow paths independently of each other or by regulation of the perfusion path supplying the hepatic artery only. In one embodiment, therefore, the flow path for the portal system may further comprises its own temperature controller, oxygenator and respiratory gas controller, pH controller, bubbletraps, and means for sensing flow rate, vascular resistance, OsM, $PaO_2$, and $PaCO_2$.

As in the hepatic artery flow path, the perfusion temperature of the portal vein flow path is maintained in the range of 25–37° C. One or more in-line oxygenators and oxygen carrier provides the oxygen tension described above for the hepatic artery and portal supplies. One or more pH electrodes, controllers and solenoid systems control the entry of $CO_2$ to maintain pH of perfusate in both flow paths in the range of 7.30–7.45.

As with other organs, long-term liver preservation is achieved by replenishing the depleted nutrients in the perfusate by perfusate exchange, dialysis, or a combination thereof, and by removing the accumulation of metabolic waste products by dialysis. The synthetic properties unique to the liver, provide regenerative opportunities by synthesizing protein and generating new cell growth.

Following either 30 minutes (n=5) or 60 minutes (n=5) of postmortem warm ischemia (WI), calf livers were excised. The suprahepatic vena cava was isolated at the diaphragm. Starting from the top left side, the livers were dissected cutting the lymphatic tissue, gastric artery and common bile duct. The portal vein and hepatic artery were isolated and cannulated with a 12 and 5 mm cannula, respectively. The livers were perfused for approximately 4 hours at 34° C. During the period of perfusion, samples of the perfusate were collected at 2 and 4 hours of perfusion for measurements of bilirubin, ALT, AST, ALP and blood gases. The contents of the gallbladder were likewise collected at 2 and 4 hours of perfusion. There was no edema or discoloration demonstrating the ability of the EMS organ culture technology to repair livers.

Livers subjected to 30 minutes of postmortem WI, all demonstrated high rates of oxygen consumption following resuscitation with EMS. When the WI insult was extended to 60 minutes, no significant difference in the rates of oxygen consumption were detected. Livers subjected to 30 minutes of postmortem WI demonstrated mean arterial pressures (MAP) of 31 mmHg (combined hepatic artery and portal vein) with corresponding combined flow rates of 320 cc/min following re-establishment of metabolism. The vascular resistance was 0.1. When the WI exposure was increased to 60 minutes postmortem, the MAP was lowered to 20 mmHg and the flow rates increased to a mean of 420 cc/min. The resulting vascular resistance was 0.06.

The standard liver function screen was performed testing for ALT, AST, Alkaline phosphatase (ALP) and total/direct bilirubin. Following resuscitation with the EMS organ culture technology, livers injured by 30 minutes of postmortem WI, except in one liver at 2 hours, demonstrated normal values of ALT, ALP and bilirubin at both time points tested (Table IV). Likewise, when the WI insult was increased to 60 minutes postmortem, after 2 and 4 hours of EMS perfusion, the ALT, ALP and bilirubin values were normal.

Bile Production

Livers resuscitated with EMS following 30 minutes of postmortem WI, produced bile throughout the period of warm perfusion. Variation in the rate of bile flow was observed, ranging from 1.5–6 cc/hr. The color of the bile was either dark green or a greenish—yellow. A normal, control consisting of bile removed from the gallbladder at the time of excision revealed 315 mg/dL of total bilirubin, 18 IU/L of ALP and was negative for AST and ALT. The livers injured by 30 minutes of postmortem WI produced bile with a wide range of bilirubin concentration—1.1–418 mg/dL(Table V). However, the mean values were close to the normal bile concentration of bilirubin. The concentration of ALP in the bile of the test livers were similar to that of normal bile. Similar to the results observed for the concentration of liver enzymes in the EMS perfusate described above, the bile AST levels decreased by half between 2 & 4 hours of perfusion in livers with 30 min WI, while the bile AST levels remained constant in the livers damaged by 60 minutes of WI. ALT was found in the bile from two of the livers following 30 minutes of WI insult at 2 hrs. of perfusion. The bile produced by livers subjected to 60 minutes of postmortem WI also contained ALT at both 2 & 4 hours of EMS perfusion. Likewise, the restored liver function was sufficient to support continuous bile production.

These results suggests that the EMS organ culture technology provides the ability to resuscitate and repair liver function following a substantial postmortem WI injury. In livers with 30 and 60 minutes of WI, metabolism was sufficiently restored with EMS perfusion to reestablish near physiologic oxygen consumption. The results of the liver function tests provide additional evidence that livers could be resuscitated from as much as 60 minutes of WI damage.

Use of EMS Technology to Provide Protection Against Cold Ischemic Damage

EMS perfusion prior to exposure to cold ischemia provides tissue protection and allows for extended periods of cold storage of an allograft. Currently, an allograft is routinely stored clinically for only 24 hours by cold storage. Extending the period of cold storage leads to a high rate in delayed function, in many cases necessitating support of the patient by dialysis until the kidney can recover function. By adapting an intact organ to an acellular perfusion prior to cold ischemic exposure, cellular protection from the cold damage is provided.

The present invention, therefore, also provides a method for storing a tissue, explant or organ intended for transplantation comprising the steps of flushing the tissue, explant or organ with a non-blood buffered physiological solution to remove blood and blood products; perfusing the tissue, explant or organ in a warm preservation system, such as the one described herein, capable of maintaining the tissue, explant or organ at a near normal rate of metabolism for a period of time sufficient to impart protection to the tissue, explant or organ; and storing the organ at 4–8° C. A period of time sufficient to impart protection is one in which the organ has had the opportunity to normalize perfusion parameters, for example, flow rate and vascular resistance. Generally, a perfusion period in the range of 30 mins to 24 hours is sufficient.

A control group of canine kidneys (n=3) were excised, immediately cold flushed with ViaSpan™ and then double bagged and stored statically packed in ice for 48 hours. The test group kidneys were placed on EMS perfusion upon excision, prior to cold storage. In this group (n=2) the excised kidneys were flushed of blood with EMS perfusion solution and placed on EMS perfusion at 32° C.–34° C. for 6 hours. After the period of EMS perfusion, the kidneys were flushed again with approximately 200cc of ViaSpan™ at 4° C. double bagged and stored statically packed in ice for 48 hours.

Just prior to reimplantation of the cold stored kidneys, the contralateral kidneys were nephrectomized. The test and control kidneys were then autotransplanted using an end-to-side anastomosis. made between the renal artery and the aorta, and the renal vein to the vena cava. Following transplantation the canine was closed and allowed to recover. Each morning the canine had blood drawn from the forelimb and chemistries were performed to determine the clinical course.

Results

EMS perfusion prior to cold storage provided for better outcomes in that the time to recovery of normal function was halved following 48 hours of static cold storage. The kidneys of the control group reperfused slowly and no urine was produced on the table. Very little urine was produced during the first evening posttransplantation. Control group dogs experienced a period of reversible acute tubular necrosis (ATN). The 24 hour posttransplant serum creatinine values were all elevated above normal values, 5.3, 2.6, & 2.8 mg/dL, respectively. The serum creatinine values continued to rise, peaked and then slowly declined, normalizing on day 7, 9 & 12 respectively.

In the test group, kidneys produced urine on the table within minutes of reperfusion. The kidneys continued to produce urine throughout the posttransplant period. The 24-hour posttransplant serum chemistries were elevated, with serum creatinine values of 2.2 & 2.5 mg/dL. In contrast to the control dogs, the peak day of elevated serum chemistries occurred on the second day posttransplant. The serum creatinine values normalized on day 5 and 6, respectively. Upon euthanasia, the kidneys appeared normal macroscopically. Histologic studies also revealed normal renal pathology.

EMS perfusion prior to reimplantation, therefore, provides protection against cold ischemia induced damage, in that the warm perfused test kidneys experience ATN that is less severe and of shorter duration. EMS perfused test group kidneys also had lower 24-hour posttransplant serum creatinine values when compared to the control group kidneys without EMS perfusion. EMS perfused kidneys also had normalized serum creatinine values sooner (5.5 vs. 9.3 days) than the control group kidneys that were immediately placed into cold storage.

Use of EMS as a Targeted Drug Delivery System

EMS perfusion can be used to deliver a drug to an organ, section of anatomy or tissue in a targeted fashion. In addition, during any procedure the EMS supported ongoing metabolism and function can be monitored providing a mechanism to quantify the impact of the drug and any corresponding cellular response to it. For example, a compound known to cause the up-regulation of the heat-shock protein, hemeoxygenase-1 was administered to an isolated kidney being perfused in accordance with the technology of the present invention. The EMS technology provided adequate support of renal metabolism and function during ex vivo perfusion to increase expression of the hemeoxygenase-1 (HO-1) enzyme within six hours.

Test group (n=3) canine kidneys were excised, cannulated, flushed of blood with EMS perfusion solution and placed on EMS perfusion at 32° C.–34° C. for 6 hours with either 5, 25 or 50 uM cobalt protoporphyrin (COPP) added to the perfusate. Metabolic and functional evaluations consisted of quantification of the ex vivo kidney function during the period of HO-1 induction. Using the EMS technology, kidneys were maintained in a metabolically active state by perfusion at near physiologic temperature. Kidneys weighing approximately 70–90 gm were procured following brain death with concomitant warm ischemia of no more than 15 minutes. The kidneys were then transitioned to EMS perfusion at 32° C. to 34° C. The kidneys were evaluated for oxidative metabolism, vascular dynamics and organ function. The organ parameters were allowed to stabilize for one hour prior to the evaluation of function. Samples from the arterial and venous lines were collected, along with the urine produced during the perfusions. $PO_2$ measurements for the arterial and venous samples were made with a Radiometer ABL5.

Oxygen consumption was calculated as:

ml/min/gm=($PO_2$ artery–$PO_2$ venous)×(flow rate).

The vascular resistance was calculated as:
vasc resis=mean arterial pressure mean flow rate

| FLOWS & METABOLISM* | | | | |
|---|---|---|---|---|
| | $O_2$Cons | F.R. | MAP | Vasc Res |
| 5 uM CoPP n = 2 | 0.18 cc/min/gm | 114 cc/min | 47 mmHg | 0.41 |
| 25 uM CoPP n = 2 | 0.23 cc/min/gm | 114 cc/min | 47 mmHg | 0.41 |
| 50 uM CoPP n = 2 | 0.17 cc/min/gm | 108 cc/min | 48 mmHg | 0.44 |

*Data Expressed as the Mean
$O_2$Cons - oxygen consumption
F.R. - vascular flow rate
MAP - mean arterial pressure
Vasc Res - vascular resistance Creatinine was added to the perfusate as a tracer. The urine made during the EMS perfusions at 32° C. to 34° C. was collected and tested. The concentration of creatinine was measured on an IDEXX Vet Lab chemistry analyzer and the glomerular filtration rate (GFR) was calculated as:

GFR=(urinary creatinine)×(urine flow). (perfusate creatinine)× (time)

The ex vivo oxidative metabolism of the kidneys was comparable with all three concentrations of CoPP and remained stable during the six hours of EMS perfusion. The restored oxidative metabolism, as measured by oxygen consumption, ranged from 0.17 to 0.23 cc/min/gm. However, the oxygen consumption was highest at all time points in the kidneys perfused with 25 $\mu$M CoPP. The perfusion pressures, vascular flow rate and the vascular resistance were also comparable in the three CoPP concentration groups. Therefor, CoPP treatment during EMS perfusion did not adversely affect the vascular dynamics or the cellular oxidative metabolism. However, differences in urine flow, creatinine clearance and development of proteinuria were observed as the concentration of CoPP induction increased.

Effect of CoPP Concentration on Organ Function

As the concentration of the CoPP was increased, the urine flow was inhibited. Urine flow was reduced by 66% when the CoPP concentration was increased from 5 to 25 $\mu$M and by >90% when the CoPP was increased to 50$\mu$M. The glomerular filtration rate (GFR) was correspondingly low since the GFR calculation is dependent upon both urine flow and urinary creatinine concentration. Increasing the CoPP concentration from 5 to 25 $\mu$M resulted in a 71% reduction of GFR. Likewise, a CoPP concentration of 50 $\mu$M led to a 91% inhibition of the GFR. An increasing concentration of CoPP was also associated with the development of "leaky endothelium" as demonstrated by proteinuria.

| ORGAN FUNCTION** | | | |
|---|---|---|---|
| | Urine Flow | GFR | Urinary Protein |
| 5 uM CoPP n = 2 | 6 cc/hr | 7.02 ml/min | 0.16 gm/dL |
| 25 uM CoPP n = 2 | 2 cc/hr | 2.05 ml/min | 3.62 gm/dL |
| 50 uM CoPP n = 2 | 0.5 cc/hr | 0.6 ml/min | 3.44 gm/dL |

*Data Expressed as the Mean
GFR - glomerular filtration rate

Up-Regulation of Hemeoxygenase-1

| | CoPP Induction During EMS Perfusion IU | | | |
|---|---|---|---|---|
| | 5 $\mu$M | 10 $\mu$M | 25 $\mu$M | 50 $\mu$M |
| kidneys | 9.6 | 16.3 | 16.1 | 15.2 |
| | 13.2 | 13.4 | 16.7 | 14.7 |

EMS perfusion effectively supported ongoing metabolism and function sufficiently for a cellular response to the CoPP leading to an increased expression of hemeoxygenase-1. Furthermore, during EMS perfusion the administration of CoPP did not adversely affect perfusion characteristics or cellular metabolism. However, organ function was found to be affected, in a dose dependant fashion as the concentration of the CoPP was increased, in terms of compromised urine flow, glomerular filtration rate and development of proteinuria. Therefore, any drug-induced toxicity can be detected during administration via EMS perfusion. At therapeutic doses, EMS perfusion was effective in supporting CoPP induction of HO-1 expression.

Use of EMS Technology for Gene Therapy

A related use of EMS technology is as a targeted gene delivery system. The long-term benefit of gene therapies is hampered by the problem of delivering the desired gene to a specific location. Organ culture technology provides a mechanism for delivering genes to the desired location. Gene therapy is particularly appealing in the context of transplanted organs because an exogenous gene can be transferred prior to transplantation. Where the pharmaceutical agent is a gene therapy vector, the construct may functionally encode for endogenous or exogenous proteins, which can then be expressed in the target after transplantation. Such gene transfer will allow for the expression of various proteins by the target tissues.

A perfusion system is particularly applicable for gene transfer and pharmaceutical administration into a number or organs, as long as the target organ has a suitable blood circulation system, for example, kidney, liver, heart and so on. The most obvious benefit of gene delivery via a perfusion system is the enhanced efficiency, target specificity for gene transfer, and the possibility of using only a small amount of vector material. Furthermore, extracorporeal perfusion systems diminish the risk of administering a large amount of foreign genetic material into the general circulation of the subject, especially important for immunocompetent individuals.

Recent attempts to deliver a gene product to an intact kidney utilizing hypothermic perfusion resulted in both reduced transfection efficiency and gene expression in target.cells (Zeigler ST, Kerby JD, Curiel DT, Diethelm AG, Thompson JA: Transpl 61:812, 1996). More importantly, the gene transfer was found to localize in the proximal tubular epithelial cells. Alterations in permeability along the vascular wall is known to be mediated by a variety of factors, including hypothermia. A consequence of altered permeability is compromised barrier function where particles normally repelled by the vascular wall by electrostatic charge or particle size have increased permeation to the substrata.

In addition to the contribution of the present invention to long-term organ preservation, the EMS technology of the present invention can be used to achieve targeted gene transfer, either ex vivo or in situ. The EMS maintains the organ or tissue to be transfected in a metabolically active state before, during and following the transfection period. The ability to interface directly with targeted tissue over extended periods of time under near physiologic conditions without exposing non-target tissues presents the opportunity to use alternative transfection procedures; including eliminating the need for viral vectors. For example, during EMS organ culture perfusion, liposome complexes or viral vectors and vascular endothelial cell-specific promoters can be introduced in the perfusion system to transfer the therapeutic DNA at a near physiologic temperature to facilitate higher incorporation rates.

An additional benefit of preserving metabolism during EMS is the feasibility of establishing the functional status of the organ or tissue prior to transfection, in contrast to using hypothermia, which inhibits metabolism and alters cell membrane potential. This is of particular importance where the organ was obtained from a donor other than a beating heart donor and may have experienced some ischemic injury. Furthermore, it is feasible to monitor the organ's metabolism during transfection, and in the case of an intact organ, to quantify the resulting organ function, i.e. diuresis, etc. Because the cell membranes are in their normal fluid state, normal barrier function is maintained providing the ability to target a gene(s) therapeutic directly to the vascular cells.

The ability of the EMS perfusion to preserve the integrity and normal barrier functions of the vessel wall within kidneys provides a mechanism for effecting transfection restricted to the vascular cells. The ability to target a gene(s) therapeutic to the vascular cells within an organ provides several important benefits. For example, the reporter gene product is in direct contact with the bloodstream, thereby providing an efficient gene therapy delivery system. Since the vascular endothelium represents the immunologic interface in organs, gene therapies present opportunities for organ specific immunomodulating therapies, in both transplantation and autoimmune diseases.

An additional benefit is that the EMS is acellular and provides the milieu for optimal transfection of a gene(s) therapeutic to the nucleus without eliciting an early immunological response. Therefore, the EMS represents a high efficiency delivery vehicle for targeted gene delivery for in situ or ex vivo application and allows for the simultaneous monitoring of metabolism and function.

In accordance with the method of the present invention, a gene of interest may be delivered to the targeted tissue via a host of currently known vehicles. Gene therapy by the homogenous recombination between exogenous DNA and the genome of the target tissue results in the modification of a particular locus within the genome. Some methods of transfection include delivery by viral vector containing the gene, liposomes, plasmid DNA and the like. Additionally, delivery of episomal DNA by the method of the invention is feasible and circumvents the need for genomic integration of the delivered gene due to episomal replication of the targeted gene vector independent of the genome.

In carrying out the targeted delivery method of the present invention on an organ or tissue, an organ containing the target tissue is isolated from a living body, is flushed of blood with warm EMS solution and then placed on EMS perfusion. The perfusion is conducted for a period of time sufficient to establish baselines of function. An exogenous molecule, for example, a viral vector, is infused into the system and perfusion continued for a period of time sufficient to deliver a pharmaceutically effective amount of the exogenous molecule. Organ function is monitored for a period of time after delivery, prior to returning the organ to a recipient.

EXAMPLE 12

A replication defective adenovirus (Adeno CMV5-GFP) encoding a green fluorescence protein (GFP) gene was used to evaluate the effectiveness of the EMS perfusion system to support gene transfer to intact bovine kidneys during ex vivo perfusion at 34° C. Bovine kidneys were flushed of blood with warm EMS solution and then placed on EMS perfusion. The perfusion was conducted for approximately 60 minutes to establish baselines of function. The viral vector ($1 \times 10_9$ PFU) was infused into the system and perfusion was continued for 2 hours. Administration of the viral vector and the resulting infectivity during EMS perfusion did not adversely affect organ metabolism or function.

Control kidneys consisted of kidneys flushed and perfused at 4° C. using a ViaSpan-based cold perfusate. Since metabolism and function are inhibited at 4° C., any effect of the viral vector on the metabolism or function of the control kidneys could not be determined.

Following the gene transfer, the kidneys were copiously flushed via the renal artery to remove any residual circulating viral particles. The lumen of the vasculature was then filled with a collagenase solution to isolate the vascular cells within each kidney and the identity of these cells was confirmed morphologically. Once the digested and isolated vascular endothelial cells were flushed from the kidneys, they were washed and placed into primary cultures at a concentration of $1 \times 10^6$ per ml. The expression of the transfected gene encoding the green fluorescence protein is described in TABLE 7.

The EMS perfusion provided for enhanced infection rates, with 40% of the vascular cells in culture expressing the GFP by 18 hours versus 17% in the cold perfused control kidneys. By 48 hours in tissue culture, the endothelial cells isolated from the EMS perfused kidneys demonstrated strong expression of the GFP in 60% of the cells. In contrast, no increased level of expression was detected in the control kidneys were the transfection was conducted in the cold.

Parenchymal cells were isolated from the EMS perfused kidneys, following the isolation of the vascular endothelial cells by collagenase digestion. The isolated parenchymal cells were found to be negative for the expression of GFP at 24 and 48 hours in tissue culture. These results suggest that the infectivity and transfer of the GFP encoding gene during EMS perfusion were limited to the vascular cells within the blood vessels of the kidneys. Therefore, better transfection rates and higher reporter gene expression was observed at both time points in the test kidneys perfused with the EMS and evidence of transfection was only found in the vascular cells.

TABLE 6

Comparison of Kidney Function Following Gene Transfer EMS Perfusion*

|  | PRE-GENE TRANSFER | POST-GENE TRANSFER |
|---|---|---|
| $O_2$ Consumption | 10.8 cc/min | 11.2 cc/min |
| Mean Arterial Pressure | 47 mmHg | 47 mmHg |
| Vascular Flow Rate | 101 cc/min | 101 cc/min |
| Diuresis | 0.4 cc/min | 0.5 cc/min |
| Glomerular Filtration Rate | 1.78 cc/min/gm | 0.7 cc/min/gm |
| Potassium Clearance | 1.78 mmol/L | 2.48 mmol/L |

*Data expressed as the mean from two kidneys

TABLE 7

| | Transfected Gene Expression* | | |
|---|---|---|---|
| Time Post Gene Transfer: | CONTROLS: VASCULAR CELLS | EMS TEST: VASCULAR CELLS | PARENCHYMAL CELLS |
| 18 Hours | 17% | 40% | 0 |
| 48 Hours | 17% | 60% | 0 |

$$\% = \frac{\text{Number of cells positive for fluorescence}}{\text{Total number of cells counted in tissue culture}}$$

The EMS warm preservation technology of the present invention preserves organs without inflicting damage and supports metabolism at a level sufficient to result in immediate normal function upon organ reimplantation (following ex vivo organ perfusion), or reperfusion (following in situ perfusion). For these reasons, EMS perfusion is particularly well suited for delivery of a therapeutic agent including, for example, in gene therapy, where delivery of a nucleotide is desired. Furthermore, the EMS warm preservation technology of the present invention provides a gene delivery/transfection system that is superior to current methodologies.

For example, U.S. Pat. No. 5,871,464, to Tryggvason et al, discloses a perfusion apparatus and methods for pharmaceutical delivery and describes successful gene transfection, both in situ and ex vivo. However, the results suggest that substantial kidney damage occurred, evidenced by excessive diuresis (800 cc during the first hour of perfusion). Additionally, diuresis increased dramatically over the second hour to 1,200 cc/hr, another indication that the kidney was damaged during the perfusion. Furthermore, the in situ perfusion did not extend past 2 hours, there was no urine production listed at subsequent times, and, in the case of ex vivo perfusion, the kidneys were not reimplanted. Thus, no post-treatment renal function is described.

It has been demonstrated that isolated kidney perfusion using the Krebs Ringers solution described in Tryggvason results in damaged organs that will not function when reimplanted. One of skill in the art will recognize that an isolated kidney is only viable for several hours when perfused at near physiologic temperature.

The improvement of EMS perfusion over that of previously reported work is that the organ is maintained at near physiologic temperature with supported organ metabolism that imparts no damage and will result in immediate normal function when reimplanted following ex vivo perfusion or reperfused following in situ perfusion. Furthermore, EMS perfusion can be performed for several days, allowing for not only efficient gene transfection while imparting no damage, but EMS can also support the organ long enough for the full expression of the gene product. The ability to support organs at near physiologic metabolism for days represents a unique ability to synthesis the protein product encoded by the transfected gene prior to reimplantation or reperfusion, something not possible with existing technology.

The following examples demonstrates the superior ability of the EMS technology to preserve organ integrity during gene delivery and transfer. Paired kidneys were excised from calves. The excised kidneys were flushed of blood, and one of the pair was placed on EMS perfusion and the other was placed on perfusion using the system and solution described by Tryggvason. During the perfusion, the oxidative metabolism was evaluated by calculating the oxygen consumption in terms of $O_2$ consumed per minute per gram, diuresis and corresponding organ function. Organ function was determined as the ability of the glomeruli to retain its normal barrier function and retain large molecules in the vascular compartment. In the case of EMS perfusion, organ function was the ability to produce urine without protein leak of the colloid, serum albumin, and since the Tryggvason patent does not include a colloid, the ability to retain the red blood cells in the vascular compartment, i.e. urine negative for red blood cells.

| Organ Preservation and Metabolism During Perfusion | | |
|---|---|---|
| | EMS Perfusion | Tryggvason Perfusion |
| Mean Pressure | 43 mmHg | 102 mmHg |
| Mean Flow Rate | 112 cc/min | 50 cc/min |
| Oxygen Consumption | 0.24 cc/min/gm | 0.10 cc/min/gm |
| Duration Stable* | >24 hours | 2 hours |
| Diuresis | 0.83 cc/hr/gm | 11.43 cc/hr/gm |
| Organ Function | negative for protein | urine hematocrit = 17% |
| Weight Gain | <10% | 57% |
| Histology | Normal blood vessels, Intact Bowman's capsules, and normal tubular Epithelium | multifocal tubular necrosis, interstitial swelling, distended and detached Bowman's capsules & endothelial necrosis |

*stability determined by stable perfusion pressures & oxygen consumption

Perfusion in accordance with the methods described in the '464 patent, that is, on a Gambro machine with an in-line oxygenator, using Krebs Ringers supplemented with red blood cells to yield a hematocrit of 17%, results in organ edema, elevated perfusion pressures as determined with a manometer, low oxygen consumption and loss of barrier function resulting in urine with a hematocrit equivalent to the perfusate. Histology provided additional data supporting the development of organ damage. In contrast, EMS perfusion prevents edema, maintains stable perfusion pressures and oxygen consumption and results in urine production that filters out protein. Histology confirmed the preserved integrity of the kidney during EMS perfusion.

| Comparison of EMS with Tryggvason Patent | | |
|---|---|---|
| | EMS | Tryggvason |
| Buffering system | yes | no |
| In-line control of pH | yes, controlled in the range of 7.30–7.40 | no, samples measured on a blood machine |
| Provides colloid osmotic support | yes | no |
| Actively supports metabolism | yes | no |
| Perfusion flow | pulsatile, controls mmHg | peristaltic, controls rate |
| Gassing system | continuous $O_2$ with intermittent $CO_2$ for pH control | standard premixed 95% $O_2$; 5% $CO_2$ |
| Organ function post-rx | normal | not determined |
| Weight gain | none | not determined |
| Organ metabolism | supported | not supported |
| Organ function | not damaged: diuresis 30–80 cc/hr stable for 48 hours urine: negative protein cleared creatinine cleared BUN | damaged: 800 cc/1st hr, 1,200 cc/2nd hr no further urine reported urine: not reported |
| When implanted | normal serum chemistries animal surviving solely on EMS treated kidney | not reimplanted, or contralateral left in place |

Long-term Preservation

EMS technology can be used to preserve organs ex vivo for extended periods in a metabolically active state and at near physiologic temperature. Using the EMS technology, 10 canine kidneys were preserved ex vivo for 24, 48 & 72 hours. During the period of ex vivo perfusion, perfusion pressures, vascular flow rate, vascular resistance, oxygen consumption, glucose consumption and diuresis remained stable. Furthermore, the kidneys appeared to be normal upon histologic evaluations. By exchanging the EMS perfusion solution, at various time points throughout the period of perfusion, adequate metabolic support was achieved. Three of these organs were reimplanted to determine subsequent viability and function.

| Organ Metabolism During EMS Perfusion | | | |
|---|---|---|---|
| | Hours of Perfusion | | |
| | 24 | 48 | 72 |
| mean perfusion pressure | 43 mmHg | 43 mmHg | 43 mmHg |
| mean flow rate | 112 cc/min | 115 cc/min | 118 cc/min |
| oxygen consumption | 0.24 cc/min/g | 0.23 cc/min/g | 0.26 cc/min/g |

Three of the kidneys perftised for >24 hours with the EMS technology were reimplanted. All three kidneys reperfused immediately with good turgor and produced urine within minutes of reperfusion. All three kidneys displayed immediate and normal function with the bladder filling by the time of closure. All three dogs survived solely on the function of the long-term EMS perfused kidneys, displaying normal serum um chemistries and urinalysis.

What is claimed is:

1. An exsanguinous metabolic support system for maintaining an isolated organ, tissue or section of anatomy in a near normal metabolic state comprising:
    (a) a non-blood perfusion solution comprising a component of the citric acid cycle wherein said perfusion solution is capable of reestablishing and supporting the vascular integrity and oxidative metabolism of an organ, thereby maintaining the organ in a functional state and at a near normal metabolic rate at warm temperatures from about 25° C. to about 37°;
    (b) a perfusion subsystem comprising one or more perfusion fluid paths for circulating said perfusion solution;
    (c) an organ chamber for holding said organ, said organ chamber being situated in said perfusion fluid path and having one or more perfusion solution inlets and support means capable of keeping the exterior of the organ from being in contact with said perfusion solution;
    (d) a controlled gassing subsystem for regulation of respiratory gases and maintenance of the pH of said perfusion solution comprising:
        (i) a first controller for continuously introducing oxygen at a constant concentration into said perfusion solution; and
        (ii) a second controller for intermittently introducing carbon dioxide into said perfusion solution wherein said second controller has a single setpoint for activation and deactivation of said second controller; and
    (e) a temperature controller for maintaining temperature of said perfusion solution at 25–37° C.

2. The exsanguinous metabolic support system of claim 1 further comprising:
    (f) a first monitoring subsystem for monitoring parameters of said perfusion solution.

3. The exsanguinous metabolic support system of claim 2 further comprising:
    (g) a second monitoring subsystem for monitoring functional parameters of an organ.

4. The system of claim 2 wherein said first monitoring subsystem for monitoring parameters of said perfusate comprises sensor means interposed in said perfusate flow path, for sensing at least one of the temperature, pH, pressure, flow rate, $PaO_2$, $PaCO_2$, and osmolarity of said perfusate.

5. The system of claim 4 wherein said first monitoring subsystem further comprises:
    a computer and said sensor means are coupled to said computer to provide the sensed information to said computer.

6. The system of claim 1, wherein said organ chamber comprises means for collecting organ product separate from perfusion solution effluent.

7. The system of claim 1 wherein said perfusion subsystem includes means for regenerating said perfusion solution.

8. The system of claim 7, wherein said means for regenerating said perfusion solution is a perfusion exchange subsystem.

9. The system of claim 8, wherein said perfusion exchange subsystem comprises a fluid exchange port, a first volume-regulatable pump in communication with said fluid exchange.port and a second volume-regulatable pump situated in a perfusion fluid path of said perfusion subsystem.

10. The system of claim 7, wherein said means for regenerating said perfusion solution is a dialysis subsystem.

11. The system of claim 10, wherein said dialysis subsystem comprises at least one nutrient reservoir in communication with an effluent reservoir via a semi-permeable membrane.

12. The system of claim 11, wherein said semi-permeable membrane has a molecular weight cutoff in the range of 1,000–80,000 daltons.

13. The system of claim 1 wherein said controlled gassing subsystem comprises sensor means interposed in said perfusate flow path for sensing pH; a controller operatively linked to said sensor means; and a solenoid operatively linked to said controller, wherein said solenoid, when activated by said controller, permits $CO_2$ gas to come into contact with said perfusion solution.

14. The system of claim 1 wherein said controlled gassing subsystem maintains pH of said perfusion solution in a range of 7.0 to 7.6.

15. The system of claim 14 wherein said controlled gassing subsystem maintains pH of said perfusion solution in a range of 7.3 to 7.45.

* * * * *